US010308693B2

(12) United States Patent
Bachnoff et al.

(10) Patent No.: US 10,308,693 B2
(45) Date of Patent: Jun. 4, 2019

(54) ANTIMICROBIAL PEPTIDES

(71) Applicant: OMNIX MEDICAL LTD., Jerusalem (IL)

(72) Inventors: Niv Bachnoff, Sede Nehemia (IL); Moshe Cohen-Kutner, Lotem (IL)

(73) Assignee: OMNIX MEDICAL LTD., Jerusalem (IL)

( * ) Notice: Subject to any disclaimer, the term of this patent is extended or adjusted under 35 U.S.C. 154(b) by 46 days.

(21) Appl. No.: 15/115,161

(22) PCT Filed: Feb. 17, 2016

(86) PCT No.: PCT/IL2016/050187
§ 371 (c)(1),
(2) Date: Jul. 28, 2016

(87) PCT Pub. No.: WO2016/132359
PCT Pub. Date: Aug. 25, 2016

(65) Prior Publication Data
US 2016/0362459 A1     Dec. 15, 2016

Related U.S. Application Data

(60) Provisional application No. 62/119,186, filed on Feb. 22, 2015.

(51) Int. Cl.
*A61K 38/00* (2006.01)
*A61K 38/17* (2006.01)
*A61K 45/06* (2006.01)
*C07K 14/435* (2006.01)

(52) U.S. Cl.
CPC .... *C07K 14/43563* (2013.01); *A61K 38/1767* (2013.01); *A61K 45/06* (2013.01); *C07K 14/43536* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 5,519,115 A * | 5/1996 | Mapelli | .................. | A01N 63/02 530/324 |
| 6,514,701 B1 * | 2/2003 | Pereira | ............... | C07K 14/4723 424/85.1 |
| 2007/0122425 A1 | 5/2007 | Keeler et al. | | |
| 2014/0296137 A1 * | 10/2014 | Rajamani | ............... | A01N 63/02 514/4.5 |

FOREIGN PATENT DOCUMENTS

WO    WO/2013039861    3/2013

OTHER PUBLICATIONS

Mika et al. (Biochimica et Biophysica (BBA)-Biomembranes; vol. 1808, Issue 9, Sep. 2011, pp. 2197-2205).*
UniProt BLAST sequence accessed Feb. 2, 2018, (<http://www.uniprot.org/blast/uniprot/B20180203AAFB7E4D2F1D05654627429E83DA5CCEEB9A415>).*
Joo ("Cyclic peptides a therapeutic agents and biochemical tools" Biomol. Ther 20 (1); 19-26 (2012).*
Gentle et al. ("Direct Production of Proteins with N-terminal cysteine for Site-Specific conjugation" Bioconjugate Chem. 2004, 15, 658-663).*
Aurora Fine Chemical (http://www.aurorafinechemicals.com/peptide-synthesis/cyclic-peptides.html; available online Sep. 11, 2008).*
Yin et al. (Cell Chemical Biology; vol. 21(4); p. 481-487, Apr. 2014).*
Rosengren, K. Johan, et al. "Cyclization of pyrrhocoricin retains structural elements crucial for the antimicrobial activity of the native peptide." Peptide Science 76.5 (2004): 446-458.
Deechongkit, Songpon, and Jeffery W. Kelly. "The effect of backbone cyclization on the thermodynamics of β-sheet unfolding: stability optimization of the PIN WW domain." Journal of the American Chemical Society 124.18 (2002): 4980-4986.
Nguyen, Leonard T., et al. "Serum stabilities of short tryptophan- and arginine-rich antimicrobial peptide analogs." PloS one 5.9 (2010): e12684.
Malik, U., et al. "In vivo efficacy of anuran trypsin inhibitory peptides against *staphylococcal* skin infection and the impact of peptide cyclization." Antimicrobial agents and chemotherapy59.4 (2015): 2113-2121.
Unger, Tamar, Ziv Oren, and Yechiel Shai. "The effect of cyclization of magainin 2 and melittin analogues on structure, function, and model membrane interactions: implication to their mode of action." Biochemistry 40.21 (2001): 6388-6397.
Wang, Guangshun. "Post-translational modifications of natural antimicrobial peptides and strategies for peptide engineering." Current biotechnology 1.1 (2012): 72-79.
Tam et al. "Disulfide bond formation in peptides by dimethyl sulfoxide." J. Am Chem. SOC. 1991, 113, 6657-6662.
Bednarek et al. "Structure-function studies on the cyclic peptide MT-11, lactum derivative of aphla-melanotropin." Peptides 20.3 (1999): 401-409; pp. 402, col. 1, para 1, p. 408, col. 1 para 2.

(Continued)

*Primary Examiner* — Jennifer Pitrak McDonald
*Assistant Examiner* — Tara L Martinez
(74) *Attorney, Agent, or Firm* — The Roy Gross Law Firm, LLC; Roy Gross

(57) ABSTRACT

The invention provides a peptide comprising: a core amino acid sequence, which is identical or similar to the amino acid sequence of a member of the Cecropin family. The invention further provides a nucleic acid sequence encoding the peptide and a vector comprising said nucleic acid. The invention further provides a pharmaceutical composition comprising said peptide or said nucleic acid.
The invention further provides methods of treating an infection, overcoming inherent or acquired resistance of a microorganism to an antibiotic agent or disinfecting a wound, the methods comprises administering the peptide to a subject in need thereof.

11 Claims, 9 Drawing Sheets

Specification includes a Sequence Listing.

(56) References Cited

OTHER PUBLICATIONS

Bulet P, et al. "Insect antimicrobial peptides: structures, properties and gene regulation" Protein and Peptide Letters, 2005, vol. 12, No. 1, pp. 3-11.
Boman et al. "Cell-Free Immunity in Insects" Annual Reviews Microbiology, 1987, vol. 41, pp. 103-126.
Hoffman, J.A., et al. "the humoral antibacterial response of *Drosophila*" Federation of European Biochemical Societies, Let., Jun. 1993, vol. 325, No. 1,2, pp. 63-66.
Bulet P, et al. "Les peptides antimicrobiens de la *drosophile*", Medicine Sciences Paris, 1999, vol. 15, No. 1, pp. 23-29.
Morishima et al. "Isolation and structure of cecropins, inducible antibacterial peptides, from the silkworm, *Bombyx mori*" Comparative Biochemistry and Physiology. B, Comparative Biochemistry, 1990. vol. 95, No. 3, pp. 551-554.
Steiner et al. "Sequence and Specificity of Two Antibacterial Proteins Involved in Insect Immunity" Nature, The Journal of Immunology, Jul. 16, 1981, vol. 292, No. 5820, pp. 246-248.
Sun et al. "Peptide sequence of an antibiotic cecropin from the vector mosquito, *Aedes albopictus*" Biochemical and Biophysical Research Communications, Sep. 1998, vol. 249, No. 2, pp. 410-415.
Bulet P, et al. "Anti-microbial peptides: from invertebrates to vertebrates" Immunological Reviews, May 2004, vol. 198, No. 1, pp. 169-184.
Caput et al. "Identification of a common nucleotide sequence in the 3'-untranslated regions of mRNA molecules specifying inflammatory mediators" Proceedings of the National Academy of Sciences of the USA, Mar. 1986, vol. 83, No. 6, pp. 1670-1674.
Lockey, T.D., et al. "Formation of pores in *Escherichia coli* cell membranes by a cecropin isolated from hemolymph of *Heliothis virescens* larvae", FEBS Feb. 15, 1996, vol. 236 (1), pp. 263-271.
Marassi, F.M., et al. Orientation of Cecropin a Helices in Phospholipid Bilayers Determined by Solid-State NMR Spectroscopy Biophysical Journal. Dec. 1999, vol. 77 (6), pp. 3152-3155.
Wang et al. "The Dependence of Membrane Permeability by the Antibacterial Peptide Cecropin B and Its Analogs, CB-1 and CB-3, on Liposomes of Different Composition" From the Department of Biochemistry, Hong Kong University of Science and Technology, Clear Water Bay, Kowloon, Hong Kong. Oct. 16, 1998, vol. 273 No. 42, pp. 27438-27448.
Boman, H.G., et al. "Cell-free immunity in Cecropia. A model system for antibacterial proteins" European Journal of Biochemistry, vol. 201, No. 1, pp. 23-31, 1991.
Bechinger et al. "Structure and Functions of Channel-Forming Peptides: Magainins, Cecropins, Melittin and Alamethicin" The Journal of Membrane Biology, Apr. 1997, vol. 156, No. 3, pp. 197-211.
Agerberth et al. "Isolation of three antibacterial peptides from pig intestine: gastric inhibitory polypeptide (7-42), diazepam-binding inhibitor (32-86) and a novel factor, peptide 3910" Eur J. Biochemistry, Sep. 1993, vol. 216, No. 2, pp. 623-629.
Jaynes et al. "In vitro cytocidal effect of lytic peptides on several transformed mammalian cell lines" Peptide research, Mar. 1, 1989, vol. 2, No. 2, pp. 157-160.
Nordeen et al. "Activity of cecropin SB37 against protoplasts from several plant species and their bacterial pathogens" Plant Science, Dec. 1992, vol. 82, No. 1, pp. 101-107.
Natori et al. "Antimicrobial proteins of insects and their clinical application" Nihon Rinsho. Japanese Journal of Clinical Medicine, May 1995, vol. 53, No. 5, pp. 1297-1304.
Okada et al. "Ionophore activity of sarcotoxin I, a bactericidal protein of Sarcophaga peregrina" Biochemical Journal, Jul. 15, 1985, vol. 229, No. 2, pp. 453-458.
Silvestro et al. "Antibacterial and Antimembrane Activities of Cecropin A in *Escherichia coli*" Antimicrobial Agents and Chemotherapy, Mar. 2000, vol. 44, No. 3, pp. 602-607.
Mitsuhara et al. "In vitro growth inhibition of human intestinal bacteria by sarcotoxin IA, an insect bactericidal peptide" Biotechnology Letters, Apr. 2001, vol. 23, No. 7, pp. 569-573.
Andrew et al. "Animal antimicrobial peptides: an overview" Biopolymers, Jan. 1998, vol. 47, No. 6, pp. 415-433.
Gunnel et al. "Characterization of inhibitor A, a protease from *Bacillus thuringiensis* which degrades attacins and cecropins, two classes of antibacterial proteins in insects" FEBS Journal, European Journal of Biochemistry, Mar. 1984, vol. 139, No. 2, pp. 247-252.
Bland et al. "Identification of Cecropin A Proteolytic Cleavage Sites Resulting from Aspergillus flavus Extracellular Protease(s)" Journal of Agricultural and Food Chemistry, Nov. 1998, vol. 46, pp. 5324-5327.
Owens et al. "A Single Amino Acid Substitution in the Antimicrobial Defense Protein Cecropin B Is Associated with Diminished Degradation by Leaf Intercellular Fluid" Molecular Plant-Microbe Interactions, 1997, vol. 10, No. 4, pp. 525-528.
International Search Report for PCT application No. PCT/IL2016/050187, dated Nov. 15, 2016.
Allefs et al. "Erwinia soft rot resistance of potato cultivars transformed with a gene construct coding for antimicrobial peptide cecropin B is not altered" American Potato Journal, Aug. 1995, vol. 72, No. 8, pp. 437-445.
Florack et al. "Expression of giant silkmoth cecropin B genes in tobacco" Transgenic Research, Mar. 1995, vol. 4, No. 2, pp. 132-141.
Hightower et al. "The expression of cecropin peptide in transgenic tobacco does not confer resistance to Pseudomonas syringae pv tabaci" Department of Plant Pathology, USA, Plant Cell Reports, Feb. 1, 1994, vol. 13, No. 5, pp. 295-299.
Bowie et al. "Deciphering the message in protein sequences: tolerance to amino acid substitutions" Science (New-York), Mar. 16, 1990, vol. 247, No. 4948, pp. 1306-1310.
Booth et al. "The use of a 'universal' yeast expression vector to produce an antigenic protein of Mycobacterium leprae" Immunology Letters, Sep. 1988, vol. 19, No. 1, pp. 65-70.
Gardella et al. "Expression of Human Parathyroid Hormone-(1-84) in *Escherichia coli* as a Factor X-cleavable Fusion Protein", The Journal of Biological Chemistry, Sep. 15, 1990, vol. 265, No. 26, pp. 15854-15859.
Fingl et al. "The Pharmacological Basis of Therapeutics", 1975, Chapter 1, p. 1.
Kanai et al. "Cloning of gene cluster for sarcotoxin I, antibacterial proteins of Sarcophaga peregrine" FEBS Letters, Dec. 1989, vol. 258, No. 2, 199-202.

\* cited by examiner

E. Coli GFPuv  0μM OMN6

Well defined intact live bacteria
GFP fluorescence detected
only inside cells

E. Coli GFPuv  50μM OMN6

Bacteria cells dead and lysed
GFP fluorescence detected
outside of cells

CTRL   OMN6

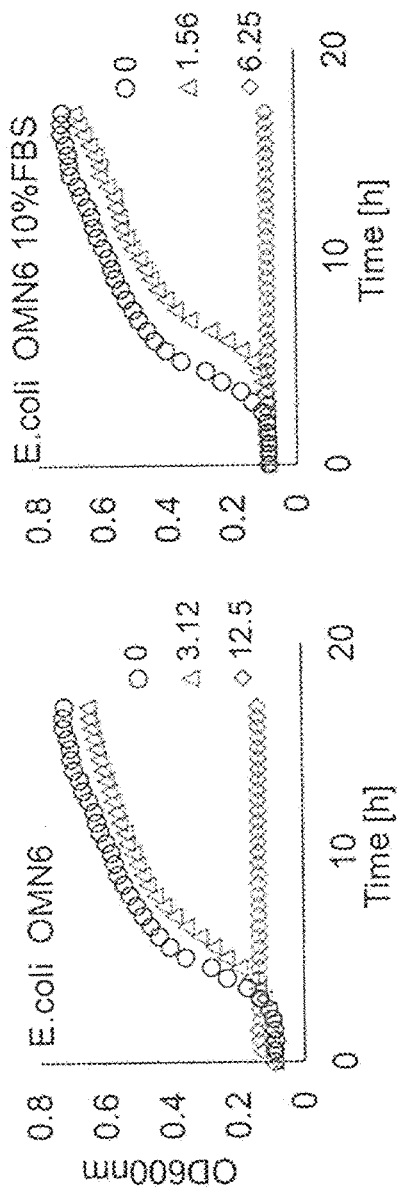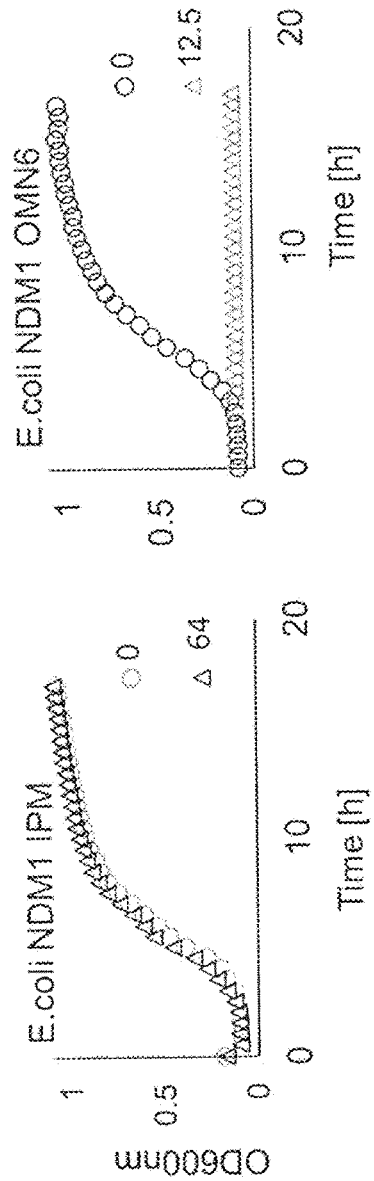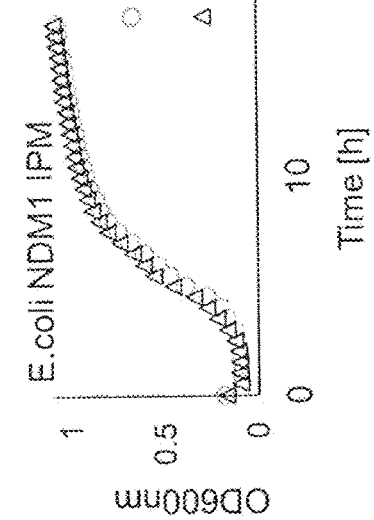

ANTIMICROBIAL PEPTIDES

CROSS-REFERENCE TO RELATED APPLICATIONS

This application is a National Phase Application of PCT International Application No. PCT/IL2016/050187, International Filing Date Feb. 17, 2016, claiming the benefit of U.S. Provisional Patent Application No. 62/119,186, filed Feb. 22, 2015 both of which are hereby incorporated by reference.

FIELD OF INVENTION

The invention encompasses antimicrobial peptides for therapeutic uses. These peptides are based on the Cecropin family which serves as potent antibacterial agents in insects.

BACKGROUND OF THE INVENTION

Antibiotics are chemical substances having the capacity, in a dilute solution, to kill or inhibit growth of microorganisms. Antibiotics that are sufficiently nontoxic to the host are used as chemotherapeutic agents to treat infectious diseases of humans, animals, and plants. The term was originally restricted to substances produced by microorganisms, but has been extended to include synthetic and semi-synthetic compounds of similar chemical activity.

Extensive and widespread use of antimicrobial drugs led to the emergence of resistant strains of microorganisms. These microorganisms are no longer susceptible to currently available antimicrobial drugs. In order to lower or prevent lethal infectious diseases and maintain public health, new antimicrobial agents are required. This forces researchers to pursue novel antibiotics, not yet resistant by bacteria. Antimicrobial peptides (AMPs) are part of the armament that insects have developed to fight off pathogens. Although usually cationic, the primary structures of insect AMPs vary markedly. Members of the most frequent AMP families adopt an α-helical conformation in membrane-mimetic environments (Bulet P. et al., Protein and *Peptide Letters*, 2005, 12, 3-11).

Insects produce antibacterial peptides, which are secreted to their hemolymph, as an innate defense against pathogenic infections (Boman, H. G. et al., *Annu. Rev. Microbial.*, 1987, 41, 103-126). Some insect species are capable of producing 10-15 different antibiotic peptides (Hoffman, J. A., et al., *FEBS Let.*, 1993, 325, 663-664). Each peptide has a complete different range of antibacterial action (Bulet, P. Medicine Sciences 1999. 15, 23-29).

Cecropins were first isolated from the hemolymph of *Hyalophora cecropia*. Cecropins are small cationic peptides consisting 29-42 amino acid residues, found in the Diptera order (genus *Drosophila, Sarcophaga*) and Lepidoptera order (genus *Hyalophora, Manduca, Bombyx, Antheraea*). It should be mentioned that a Cecropin was isolated from porcine intestine (Boman, H. G., et al. Eur. J. Biochem. 1991. 201, 23-31; Morishima, I., et al. Biochem. Physiol. 1990. 95B, 551-554; Steiner, H., et al. Nature 1981. 292, 246-248; Sun, D., et al. Biochem. Biophys. Res. Commun 1998. 249(2), 410-415; Bulet, P. et al Immunological Reviews. 2004. 198, 169-184). The known sequences for the major Cecropins show that the N-terminal parts are strongly basic while the C-terminal regions are neutral and contain long hydrophobic stretches. In all cases the Cecropins have an amidated C-terminal residue (Boman, H. G. et al., *Annu. Rev. Microbial.*, 1987, 41, 103-126). Cecropins secondary structure forms two amphiphatic α-helices which are able to penetrate the bacterial membrane. This ability is followed by membrane loss of ionic gradient balance leading to bacterial death (Christensen, B. C., et al. Proc. Natl. Acad. Sci. USA. 1988 83:1670-1674; Lockey, T. D., et al. Eur. J. Biochem. 1996. 236, 263-271; Marassi, F. M., et al. Biophys. J. 1999. 77, 3152-3155; Wang, W., et al. *J. Biol. Chem.* 1998. 273, (42) 27438-27448).

Cecropins are very similar molecules as half the amino acid substitutions are strictly conservative. Theoretical predictions and circular dichroism spectra indicate that these peptides can form nearly perfect amphipathic α-helices with charged groups on one longitudinal side and hydrophobic side residues on the opposite side. Proteins with amphipathic helices are often associated with membranes, and this secondary structure may be of importance for the membrane-disrupting activity of the Cecropins (Boman, H. G. et al., *Annu. Rev. Microbial.*, 1987, 41, 103-126).

The structure of different sequences of peptides of the Cecropin family shows that they represent similar types of molecules. In addition to strongly basic N-terminal region and a long hydrophobic stretch in the C-terminal half, there are other typical conserved features such as: tryptophan at position 2, the single and double lysines at positions 5, 8 and 9 and arginine at position 12. It can be concluded that there must have been strong selection pressures that have conserved certain Cecropin sequences in different types of insects throughout evolution (Boman, H. G., et al. Eur. J. Biochem. 1991. 201, 23-31).

Membrane-active peptides exhibit channel-like conductivities across planar lipid bilayer systems as well as bilayer disruption. These bilayer openings deprive the affected organisms of their transmembrane electrochemical gradients, resulting in increased water flow concomitant with cell swelling, osmolysis and cell death. Antimicrobial peptides of particular interest for pharmacological applications are those which manifest antibacterial activity, but under the same conditions, do not show hemolytic or cytotoxic effect against healthy vertebrate cells (B. Bechinger. et al. J. Membrane Biol. 1997. 156, 197-211). Most antibacterial peptides have to be positively charged in order to bind to bacterial surfaces, which normally are negatively charged. Cecropins show strong antibiotic activity against a variety of Gram-negative and Gram-positive bacteria without lysing mammalian cell lines or yeast (Agerberth, B. et al. Eus. J. Biochem. 1993. 216, 623-629).

The cell killing activity of Cecropins is not mediated through specific, chiral receptor interactions. The cell lytic activity of these peptides correlates with their ability to form α-helical secondary structures in membrane environments as well as with their binding affinity to liposomes (B. Bechinger. et al. J. Membrane Biol. 1997. 156, 197-211). Toxicity studies on a variety of cell types have shown that, although plant protoplasts are more sensitive to Cecropins than are animal cells, plant cells are one to two orders of magnitude less sensitive to these peptides than their bacterial pathogens (Jaynes, J. M., et al. Peptide Res. 1989. 2, 157-160; Nordeen, R. D., et al. Plant Sci. 1992. 82, 101-107).

A strong example for Cecropin advantage as antimicrobial agents can be found in Cecropin A. Cecropin A, a 37-residue peptide, is composed entirely of ordinary L-amino acids (Steiner H., et al. Nature. 1981, 292:246-248). Cecropin A secondary structure is composed of two amphiphatic α-helixes with an identical length of bacterial plasma membrane. The primary target of this toxin is assumed to be the microbial membrane, and its antimicrobial effect is probably due to ionophore activity. When *Escherichia coli* bacteria were treated with Cecropin A, K+ ions inside of the cells leaked out rapidly and the ATP pool of the cells rapidly decreased. These results suggested that the bactericidal effect of Cecropin A was due to its ionophore activity, and that it blocked the generation of ATP by inhibiting formation of the proton gradient essential for oxidative phosphorylation (Natori, S. Nippon Rinsho. 1995. 53, 1297-1304; Okada, M., et al. Biochem. J. 1985.229, 453-458, Silvestro L. et al. Antimicrob Agents Chemother. 2000 March; 44(3): 602-607).

It should be noted that Cecropins inhibited the growth of harmful bacteria in the human intestine without affecting the growth of beneficial bacteria which are abundant in the intestines of healthy people (Mitsuhara, I., et al. Biotechnology Letters. 2001. 23, 569-573).

The use of peptides as antibiotics is not obvious due to their sensitivity to protease activity (Andrew, D., et al. Biopolymers. 1998.47, 415-433). Most Cecropins are rich with Lysine and Arginine residues, which commonly comprise part of target sequences for abundant proteases such as trypsin, Inhibitor A and Proteinase K (Gunnel DALHAMMAR et al. Eur. J. Biochem. 139, 247-252 (1984, Bland J M et al. Journal of agricultural and food chemistry 1998 v. 46 no. 12 pp. 5324-5327). Previous research has shown that Cecropins are rapidly degraded in the intracellular fluid of plants (Owens, L. D., et al. Mol. Plant Microbe Interact. 1997. 10, 525-528). Several experiments trying to express Cecropins in plants have failed probably due to sensitivity to proteolytic activity (Allefs, S. J. H. M., et al. Am. Potato J. 1995. 72, 437-445; Florack, D., et al. Transgenic Res. 1995. 4, 132-141; Hightower, R., et al. Plant Cell Rep. 1994. 13, 295-299).

The engineering of stable proteins is of great technological and economic importance, since the limited stability of proteins often severely restricts their medical and industrial application. It is therefore an object of the invention to provide novel stable peptide-based antibiotics, such as AMCP's.

SUMMARY OF THE INVENTION

The present invention provides genetically engineered or synthesized degradation-resistant, peptides. In some embodiments, the peptides comprise at least one cysteine residue at their carboxy- and amino-terminus. In some embodiments of the invention, under oxidative environment, e.g. as in various infections, the cysteines in the carboxy- and amino-terminus of the peptides of the invention, are covalently bonded, thus creating in an embodiment of the invention a cyclic form of the peptides, wherein said cyclic peptides represent higher stability while maintaining its original biological activity.

The present invention relates to a peptide comprising a core amino acid sequence, which is identical or similar to the amino acid sequence of a member of the Cecropin family, wherein the core amino acid sequence is extended at the N-terminus by an N-terminal group and/or extended at the C-terminus by a C-terminal group; and wherein the N-terminal group and/or the C-terminal group are identical or different and are capable of forming a covalent bond so as to form a cyclic peptide or a homomultimer assembly via intermolecular covalent linkage.

In some embodiments of the invention, the member of the Cecropin family belongs to the group of AMP $CM_{IV}$, Cecropin A, Cecropin B, Cecropin B2, Cecropin D, Cecropin IA, and Cecropin P1.

In some embodiments of the invention, the cyclic peptide has a topology, wherein the topology is head-to-tail, side-chain-to-side-chain, head-to-side-chain or side-chain-to-tail or backbone-to-backbone or side-chain-to-backbone or head-to-backbone or tail-to-backbone.

In some embodiments of the invention, the covalent linkage is formed under oxidative and/or acidic physiological conditions.

In some embodiments of the invention, the amino acid sequence of the member of the Cecropin family comprises 17-144 amino acids.

In some embodiments of the invention, the core amino acid sequence of a member of the Cecropin family is as set forth in SEQ ID Nos. 12-22.

In some embodiments of the invention, the core amino acid sequence has at least 70%, 75%, 80%, 85%, 90%, 95% or 99% sequence identity to the amino acid sequences set forth in SEQ ID Nos. 12-22.

In some embodiments of the invention, the core amino acid sequence comprising substitution, conservative amino acid substitutions, conservatively modified sequence variants, deletion, and/or insertion at one or more position.

In some embodiments of the invention, the C-terminus group and/or the N terminus group comprises one or more of cysteine, cysteine derivative, an amino acid sequence, which contains cysteine or a group comprising a thiol moiety or any combination thereof.

In some embodiments of the invention, the C-terminus group and/or the N terminus group are each selected from the group consisting of cysteine, cysteine derivative, an amino acid sequence which contains cysteine or any other group comprising a thiol moiety.

In some embodiments of the invention, the N-terminus group comprises the amino acid sequence methionine-cysteine, methionine-cysteine derivative, methionine derivative-cysteine or methionine derivative-cysteine derivative and the C-terminus group is cysteine or a cysteine derivative.

In some embodiments of the invention, the C-terminus group comprises the amino acid sequence methionine-cysteine, methionine-cysteine derivative, methionine derivative-cysteine or methionine derivative-cysteine derivative and the N-terminus group is cysteine or a cysteine derivative In some embodiments of the invention, the covalent linkage is a disulfide bond.

In some embodiments of the invention, the covalent linkage is an amide, lactam or peptide bond.

In some embodiments of the invention, the N-terminus group and the C-terminus group are covalently bound so as to form a cyclic peptide.

In some embodiments of the invention, the peptide is self-assembled within a physiological membrane such that the intermolecular covalent linkage is formed between the N-terminus group of the peptide to the N-terminus or a C-terminus group of an additional identical peptide or wherein the intermolecular covalent linkage is formed between the C-terminus group of the peptide to the N-terminus or a C-terminus groups of an additional identical peptide.

In some embodiments of the invention, the peptide is as set forth in any one of SEQ ID Nos. 1-11.

In some embodiments of the invention, the peptide has an amino acid sequence which is at least 70%, 75%, 80%, 85%, 90%, 95% or 99% sequence identity to the amino acid sequences set forth in SEQ ID Nos. 1-11.

In some embodiments of the invention, the peptide is as set forth in SEQ ID NO: 6.

In some embodiments of the invention, the peptide has an amino acid sequence which is at least 70%, 75%, 80%, 85%, 90%, 95% or 99% sequence identity to the amino acid sequence set forth in SEQ ID NO: 6.

The present invention relates to a nucleic acid sequence encoding any one of the above referenced peptides.

The present invention relates to a vector comprising the above referenced nucleic acid.

The present invention relates to a pharmaceutical composition comprising any one of the above referenced peptides or the above referenced nucleic acid.

The present invention relates to a method of treating an infection, the method comprising administering and one of the above referenced peptides or the above referenced pharmaceutical composition to a subject in need thereof.

The present invention relates to a use of any one of the above referenced peptides or the above referenced pharmaceutical composition in the preparation of a medicament for treating an infection in a subject.

In some embodiments of the invention, the infection is bacterial, viral- and/or fungal infection.

In some embodiments of the invention, the pharmaceutical composition is in a form of a liquid, cream, gel, paste, powder, emulsion, an ointment, a liniment, a lotion, a transdermal system, an injection fluid, a suspension, a patch film patch or spray.

In some embodiments of the invention, the pharmaceutical composition is in the form of capsule or a tablet.

In some embodiments of the invention, the composition or the peptide is administered in conjunction with one or more additional anti-inflammatory active agent.

The present invention relates to a method of overcoming inherent or acquired resistance of a microorganism to an antibiotic agent, comprising: contacting the microorganism to any one of the above referenced peptides or the above referenced pharmaceutical composition.

In some embodiments of the invention, the microorganism is *Escherichia coli, Klebsiella Pneumoniaea, Pseudomonas aeruginosa, Salmonella* serotype *Typhi, Acinetobacter baumannii*, a member of Enterobacteriaceae spp., *Pseudomonas* spp. *Salmonella* spp., or *Acinetobacter* spp., or any combination thereof.

The present invention relates to a method of disinfecting a wound comprising contacting the wound with any one of the above referenced peptides or the above referenced pharmaceutical composition.

In some embodiments of the invention, the wound is a blister wound, a soft tissue wound, a cutaneous abscess, a surgical wound, a sutured laceration, a contaminated laceration, a burn wound, a decubitus ulcer, a stasis ulcer, a leg ulcer, a foot ulcer, a venous ulcer, a diabetic ulcer, an ischemic ulcer, a pressure ulcer, an oral infection, a periodontal disease, a partial thickness burn, or a full thickness burn.

BRIEF DESCRIPTION OF THE FIGURES

FIG. 3: is a photograph showing Green Fluorescent Protein (GFP) leaking from lysed bacteria cells.

FIG. 6A: *E. coli* bacteria growth monitored over 17.5 hours via absorbance at 600 nm Bacteria growth or inhibition of growth is presented as OD600 nm values over time.

As the bacteria grow, OD values increase. A dose-response of OMN6 antimicrobial effect is demonstrated by the decreased OD values that represent bacterial death in correlation with increasing OMN6 concentration in μM.

FIG. 6B: The same experimental system as described for FIG. 6A was applied, with the addition of 10% Fetal Bovine Serum (FBS). This addition of FBS serves to better represent the environment existing in-vivo and predict the ability of OMN peptides to exert their effect in live animals and later in the human body FIGS. 6C and 6D: The same experiment was conducted with *E. coli* NDM-1 bacteria, an Imipenem (IPM) resistant strain. IPM concentration is given in μg/ml. FIG. 6C clearly shows that IPM has lost its inhibitory effect on bacteria growth as a result of the bacteria resistance. In FIG. 6D OMN6 exerts a powerful antimicrobial effect on this resistant strain. These results show that OMN6 is an effective antimicrobial agent against drug-resistant bacteria, on which a treatment with conventional antibiotics has failed.

Figure 7:
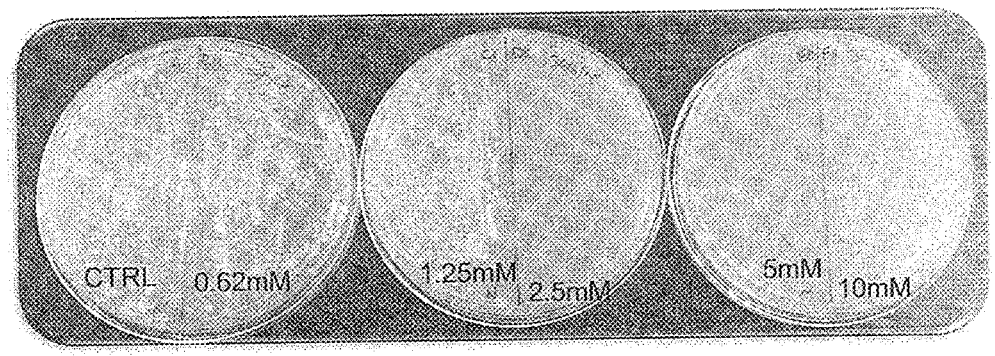

FIG. 7: is a picture depicting an example of the antimicrobial effect of OMN6 on resistant bacteria. Multi Drug Resistant *A. baumannii* bacteria was plated on appropriate medium and incubated for 24-48 hours to allow the growth of colonies. Prior to plating, bacteria were incubated with OMN6 at increasing concentrations of between 0-10 μM (see also in FIG. 8), and monitored as previously described (FIG. 6 and Example 5).

Bacteria in CTRL, when plated, yielded countless colonies, showing that their growth has not been inhibited. When OMN6 treated bacteria were plated, the medium remained clear and no colonies were seen. The absence of colonies indicates that all the bacteria were killed as a result of the treatment with OMN6.

Figure 8:
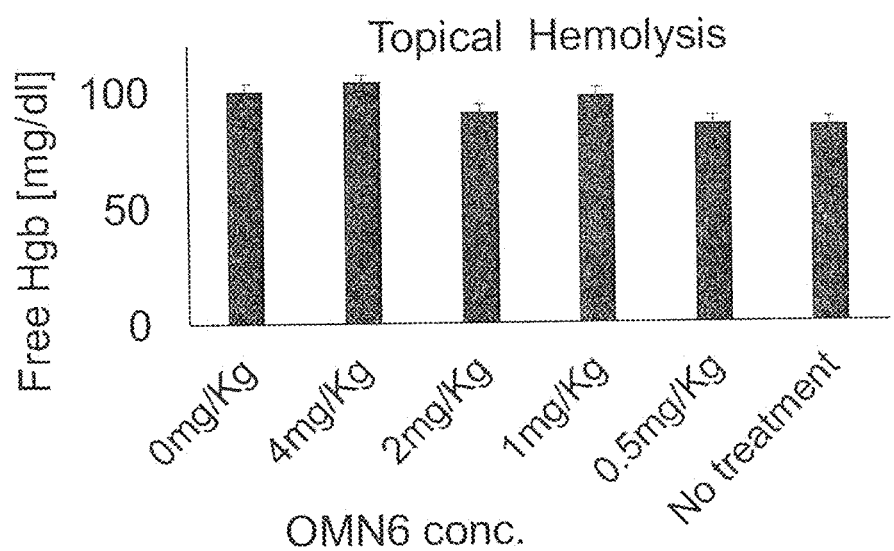

FIG. 8: is an overview of the preliminary topical safety experiment in mice as detailed in Table 9. All the groups and treatments are presented as well as all the analysis assays performed. The figure depicts the results from the analysis of the hemolysis assay conducted. The figure depicts the quantification of Free-Hemoglobin averaged for each experimental group and presented as percent of the control group (%/CTRL).

Figure 9:
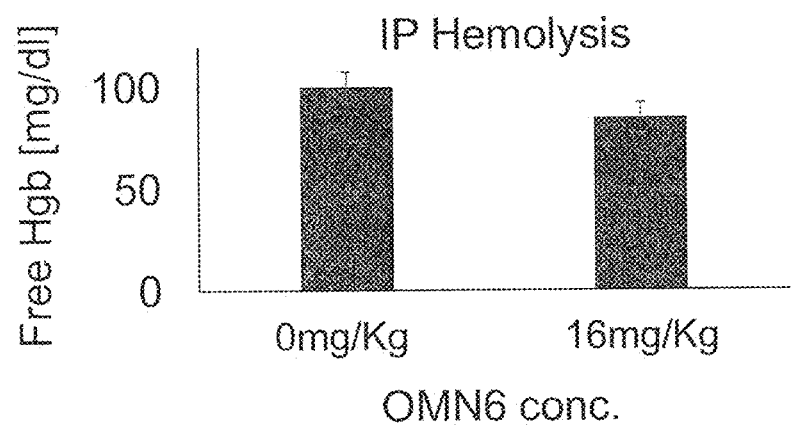

FIG. 9: Is an overview of the preliminary intraperitoneal (IP) injection safety experiment in mice as detailed in Table 10. All the groups and treatments are presented as well as all the analysis assays performed. This Figure shows the results from the analysis of the hemolysis assay conducted. The figure depicts the quantification of Free-Hemoglobin averaged for each experimental group and presents it as % of CTRL.

Figure 10A:
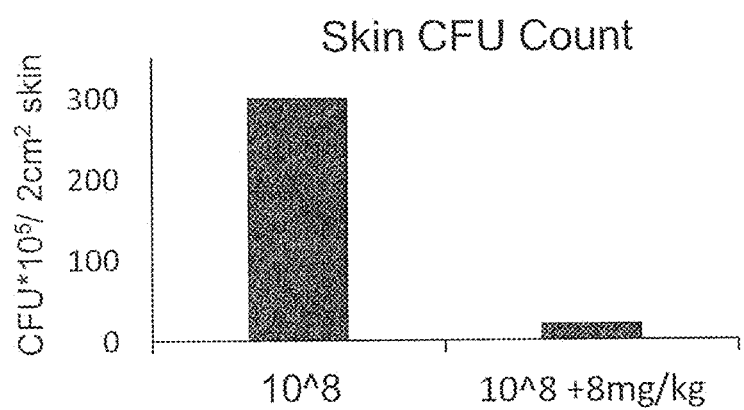
Figure 10B:
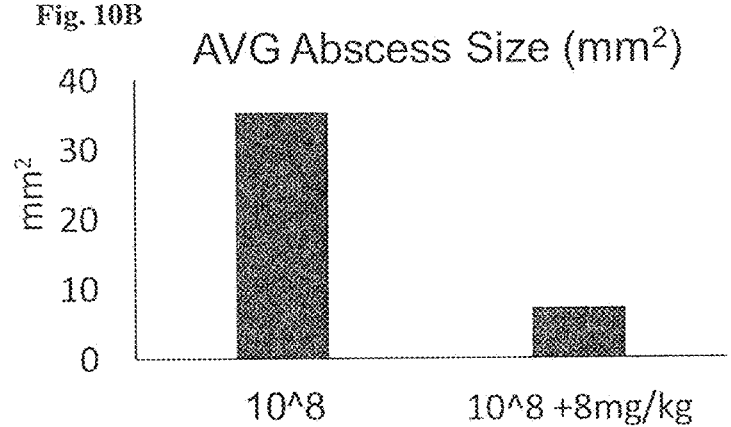

FIG. 10 summarizes the results of an experiment conducted to evaluate the efficacy of OMN6 in-vivo. Mice were injected subcutaneously (SC) with $10^8$ Colony Forming Units (CFU)/mouse of *E. coli* ESBL, a resistant strain. Experiment group was treated with OMN6 at a concentration of 8 mg/kg and CTRL group was treated with saline (0.9% NaCl) solution as a sham treatment. After four days, mice were sacrificed and skin samples were analyzed for bacterial burden (FIG. 10A) and abscess size in $mm^2$ (FIG. 10B). Results show that the bacterial burden was lowered by 94% in the group treated with OMN6. Abscess size was decreased by 80% in the group treated by OMN6. Considering these results, it is clear that OMN6 is exerting a strong antimicrobial effect and is highly efficient in-vivo.

DETAILED DESCRIPTION OF THE EMBODIMENTS OF THE INVENTION

The invention is based on peptides from the Cecropin family, which are expressed mainly in insects from the Lepidoptera and Diptera orders.

The present invention provides, degradation-resistant, peptides that can be used as antibiotic medicmants. In some embodiments, the peptides comprise at least one cysteine residue at their carboxy- and amino-terminus. In some embodiments of the invention, under oxidative environment, e.g. as in various infections, the cysteines in the carboxy- and amino-terminus of the peptides of the invention, are covalently bonded, thus creating a cyclic form of the peptides, wherein said cyclic peptides represent higher stability while maintaining its original biological activity.

In some embodiments, there is provided a peptide comprising: a core amino acid sequence, which is identical or similar to the amino acid sequence of a member of the Cecropin family, wherein the core amino acid sequence is extended at the N-terminus by an N-terminal group and/or extended at the C-terminus by a C-terminal group; and wherein the N-terminal group and/or the C-terminal group are identical or different or null and are capable of forming a covalent bond so as to form a cyclic peptide or a homomultimer assembly via intermolecular covalent linkage.

As used herein, in one embodiment the phrase "homomultimer assembly" refers to molecular structural organization comprising more than one replica of the same molecule. The connectivity and structural organization of the different replicas of the same molecule could be maintained via covalent bond and/or non covalent interactions.

As used herein, in one embodiment the phrase "intermolecular covalent linkage" refers to covalent bond that is formed between two identical or different molecules.

In some exemplary embodiments of the invention, the member of the Cecropin family belongs to the group of AMP CMIV, Cecropin A, Cecropin B, Cecropin B2, Cecropin D, Cecropin IA, and Cecropin P1.

Reference is made to Tables 1, 2 and 3 which show a library of 11 exemplary antimicrobial peptides of the invention (sequences 1-11, Table 1), the original sequences from the Cecropin family (sequences 12-22, Table 2), and nucleic acid sequences encoding the peptides as set forth in SEQ ID Nos. 1-11, Table 3).

Table 1 presents the amino acid sequence of the modified peptides. Inserted cysteine and methionine residues appear in bold.

TABLE 1

Omnix Medical Modified Peptides

| Name | Sequence ID | Species origin/ Original Cecropin | Amino acid sequence |
| --- | --- | --- | --- |
| OMN 1 | SEQ ID NO: 1 | *S. peregrina* Cecropin IA | MCGWLKKIGKKIERVGQHTRDA TIQGLGIAQQAANVAATARGC |
| OMN 2 | SEQ ID NO: 2 | *H. cecropia* Cecropin B | MCKWKVFKKIEMKGRNIRNGIV KAGPAIAVLGEAKALC |

TABLE 1-continued

Omnix Medical Modified Peptides

| Name | Sequence ID | Species origin/ Original Cecropin | Amino acid sequence |
|---|---|---|---|
| OMN 3 | SEQ ID NO: 3 | *M. sexta* Cecropin B-2 | MCWNPFKELERAGQRVRDAVTS AAPAVATVGQAAAIARC |
| OMN 4 | SEQ ID NO: 4 | *H. cecropia* Cecropin D | MCWNPFKELEKVGQRVRDAVIS AGPAVATVAQATALAKC |
| OMN 5 | SEQ ID NO: 5 | *A. pernyi* Cecropin D | MCWNPFKELERAGQRVRDAIISA GPAVATVAQATALAKC |
| OMN 6 | SEQ ID NO: 6 | *H. cecropia* Cecropin A | MCKWKLFKKIEKVGQNIRDGIIK AGPAVAVVGQATQIAKC |
| OMN 7 | SEQ ID NO: 7 | *B. mori* AMP CM$_{IV}$ | MCRWKIFKKIEKVGQNIRDGIVK AGPAVAVVGQAATIC |
| OMN 8 | SEQ ID NO: 8 | *B. mori* Cecropin A | MCRWKIFKKIEKMGRNIRDGIVA AGPAIEVLGSAKAIC |
| OMN 9 | SEQ ID NO: 9 | *A. pernyi* Cecropin B | MCKWKIFKKIEKVGRNIRNGIIK AGPAVAVLGEAKALC |
| OMN 10 | SEQ ID NO: 10 | *D. melanogaster* Cecropin A | MCGWLKKIGKKIERVGQHTRDA TIQGLGIAQQAANVAATARC |
| OMN 11 | SEQ ID NO: 11 | *S.s. domesticus* Cecropin P1 | MCSWLSKTAKKLENSAKKRISE GIAIAIQGGPRC |

Table 2 presents the amino acid sequences of exemplary peptides from the Cecropin family and their origin.

Table 3 presents the nucleic acid sequences encoding respectively the peptides of sequences 1-11.

TABLE 2

Cecropin Family of Peptides

| Sequence ID | Species origin | Original Cecropin | Amino acid sequence |
|---|---|---|---|
| SEQ ID NO: 12 | *S. peregina* | Cecropin IA | GWLKKIGKKIERVGQHTRDA TIQGLGIAQQAANVAATARG |
| SEQ ID NO: 13 | *H. cecropia* | Cecropin B | KWKVFKKIEMKGRNIRNGIV KAGPAIAVLGEAKAL |
| SEQ ID NO: 14 | *M. sexta* | Cecropin B-2 | WNPFKELERAGQRVRDAVTS AAPAVATVGQAAAIAR |
| SEQ ID NO: 15 | *H. cecropia* | Cecropin D | WNPFKELEKVGQRVRDAVIS AGPAVATVAQATALAK |
| SEQ ID NO: 16 | *A. pernyi* | Cecropin D | WNPFKELERAGQRVRDAIIS AGPAVATVAQATALAK |
| SEQ ID NO: 17 | *H. cecropia* | Cecropin A | KWKLFKKIEKVGQNIRDGII KAGPAVAVVGQATQIAK |
| SEQ ID NO: 18 | *B. mori* | AMP CM$_{IV}$ | RWKIFKKIEKVGQNIRDGIV KAGPAVAVVGQAATI |
| SEQ ID NO: 19 | *B. mori* | Cecropin A | RWKIFKKIEKMGRNIRDGIV AAGPAIEVLGSAKAI |
| SEQ ID NO: 20 | *A. pernyi* | Cecropin B | KWKIFKKIEKVGRNIRNGIIK AGPAVAVLGEAKAL |
| SEQ ID NO: 21 | *D. melanogaster* | Cecropin A | GWLKKIGKKIERVGQHTRDA TIQGLGIAQQAANVAATAR |
| SEQ ID NO: 22 | *S.s. domesticus* | Cecropin P1 | SWLSKTAKKLENSAKKRISE GIAIAIQGGPR |

TABLE 3

Nucleotide Sequence encoding the modified peptides of the invention.

| Name | Sequence ID | Species origin/ Original Cecropin | Nucleotide sequence |
|---|---|---|---|
| OMN 1 | SEQ ID NO: 23 | S. peregrina Cecropin IA | atgtgcggctggctgaaaaaaattggc aaaaaaattgaacgcgtgggccagcat acccgcgatgcgaccattcagggcctg ggcattgcgcagcaggcggcgaacgtg gcggcgaccgcgcgcggctgc |
| OMN 2 | SEQ ID NO: 24 | H. cecropia Cecropin B | atgtgcaaatggaaagtgtttaaaaaa attgaaaaaatgggccgcaacattcgc aacggcattgtgaaagcgggcccggcg attgcggtgctgggcgaagcgaaagcg ctgggctgc |
| OMN 3 | SEQ ID NO: 25 | M. sexta Cecropin B-2 | atgtgctggaacccgtttaaagaactg gaacgcgcgggccagcgcgtgcgcgat gcggtgattagcgcggcgccggcggtg gcgaccgtgggccaggcggcggcgatt gcgcgcggctgc |
| OMN 4 | SEQ ID NO: 26 | H. cecropia Cecropin D | atgtgctggaacccgtttaaagaactg gaaaaagtgggccagcgcgtgcgcgat gcggtgattagcgcgggcccggcggtg gcgaccgtggcgcaggcgaccgcgctg gcgaaaggcaaatgc |
| OMN 5 | SEQ ID NO: 27 | A. pernyi Cecropin D | atgtgctggaacccgtttaaagaactg gaacgcgcgggccagcgcgtgcgcgat gcgattattagcgcgggcccggcggtg gcgaccgtggcgcaggcgaccgcgctg gcgaaatgc |
| OMN 6 | SEQ ID NO: 28 | H. cecropia Cecropin A | atgtgcaaatggaaactgtttaaaaaa attgaaaaagtgggccagaacattcgc gatggcattattaaagcgggcccggcg gtggcggtggtgggccaggcgacccag attgcgaaaggctgc |
| OMN 7 | SEQ ID NO: 29 | B. mori AMP CM$_{IV}$ | atgtgccgctggaaaattttaaaaaa attgaaaaagtgggccagaacattcgc gatggcattgtgaaagcgggcccggcg gtggcggtggtgggccaggcggcgacc atttgc |
| OMN 8 | SEQ ID NO: 30 | B. mori Cecropin A | atgtgccgctggaaaattttaaaaaa attgaaaaaatgggccgcaacattcgc gatggcattgtgaaagcgggcccggcg attgaagtgctgggcagcgcgaaagcg attggcaaatgc |
| OMN 9 | SEQ ID NO: 31 | A. pernyi Cecropin B | atgtgcaaatggaaaattttaaaaaa attgaaaaagtgggccgcaacattcgc aacggcattattaaagcgggcccggcg gtggcggtgctgggcgaagcgaaagcg ctgtgc |
| OMN 10 | SEQ ID NO: 32 | D. melanogaster Cecropin A | atgtgcagcgaagcgggctggctgaaa aaaattggcaaaaaaattgaacgcgtg ggccagcatacccgcgatgcgaccatt cagggcctgggcattgcgcagcaggcg gcgaacgtggcggcgaccgcgcgcggc tgc |
| OMN 11 | SEQ ID NO: 33 | S.s. domesticus Cecropin P1 | atgtgcagctggctgagcaaaaccgcg aaaaaactggaaaacagcgcgaaaaaa cgcattagcgaaggcattgcgattgcg attcagggcggcccgcgctgc |

In some embodiments of the invention, the cyclic peptide has a topology, wherein the topology is head-to-tail, side-chain-to-side-chain, head-to-side-chain or side-chain-to-tail or backbone-to-backbone or side-chain-to-backbone or head-to-backbone or tail-to-backbone. The cyclic peptide according to some embodiments of the invention is homodetic cyclic peptide, cyclic isopeptide, cyclic depsipeptide or bicyclic peptide. In some embodiments, the covalent linkage is formed under oxidative and/or acidic physiological conditions. In some embodiments, the peptide of the invention is a stapled peptide.

As used herein, in one embodiment relating to the topology of the cyclic peptide, the phrase "head-to-tail" refer to cyclization of the peptide via amide bond formation between the amino terminus and the carboxyl terminus of the peptide.

As used herein, in one embodiment relating to the topology of the cyclic peptide, the phrase "side-chain-to-side-chain" refers to cyclization of the peptide via the formation of covalent bond between two side chains.

As used herein, in one embodiment relating to the topology of the cyclic peptide, the phrase "head-to-side-chain" refers to cyclization of the peptide via the formation of covalent bond between the amino terminus and a side chain of the peptide.

As used herein, in one embodiment relating to the topology of the cyclic peptide, the phrase "side-chain-to-tail" refers to cyclization of the peptide via the formation of covalent bond between the carboxyl terminus and a side chain of the peptide.

As used herein, in one embodiment relating to the topology of the cyclic peptide, the phrase "backbone-to-backbone" refers to cyclization of the peptide via the formation of covalent bond between two different backbone atoms of the peptide.

As used herein, in one embodiment relating to the topology of the cyclic peptide, the phrase "side-chain-to-backbone" refers to cyclization of the peptide via the formation of covalent bond between a side chain and a backbone atom of the peptide.

As used herein, in one embodiment relating to the topology of the cyclic peptide, the phrase "head-to-backbone" refers to cyclization of the peptide via the formation of covalent bond between the amino terminus and a backbone atom of the peptide.

As used herein, in one embodiment relating to the topology of the cyclic peptide, the phrase "tail-to-backbone" refers to cyclization of the peptide via the formation of covalent bond between the carboxyl terminus and a backbone atom of the peptide.

In some embodiments, the core amino acid sequence of a member of the Cecropin family is as set forth in SEQ ID Nos: 12-22 as detailed in Table 2. The core amino acid sequence may comprise of L or D stereoisomers or combination thereof. In some embodiments of the invention, the core amino acid sequence has at least 70%, 75%, 80%, 85%, 90%, 95% or 99% sequence identity to the amino acid sequences set forth in SEQ ID Nos: 12-22. The core amino acid sequence may comprise according to some embodiments, substitution, conservative amino acid substitutions, conservatively modified sequence variants, deletion, and/or insertion at one or more position or is in reverse order.

As used herein, in one embodiment the phrase "conservative amino acid substitutions" or the phrase "conservatively modified sequence variant" refer to trivial changes in amino acid sequence were one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified sequence variant", including where the alteration results in the substitution of an amino acid with a chemically similar amino acid (conservative amino acid substitutions). Conservative substitution tables providing functionally similar amino acids are well known in the art. Guidance concerning which amino acid changes are likely to be phenotypically silent can also be found in Bowie et al., 1990, Science 247: 1306 1310. Such conservatively modified variants are in addition to and do not exclude polymorphic variants, interspecies homologs, and alleles. Typical conservative substitutions include but are not limited to: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). Amino acids can be substituted based upon properties associated with side chains, for example, amino acids with polar side chains may be substituted, for example, Serine (S) and Threonine (T); amino acids based on the electrical charge of a side chains, for example, Arginine (R) and Histidine (H); and amino acids that have hydrophobic side chains, for example, Valine (V) and Leucine (L). As indicated, changes are typically of a minor nature, such as conservative amino acid substitutions that do not significantly affect the folding or activity of the protein.

In some embodiments of the invention, the amino acid sequence of the member of the Cecropin family which forms the core amino acid of the peptide of the invention comprises 17-144 amino acids. In some embodiments of the invention, the amino acid sequence of the member of the Cecropin family comprises 20-140 amino acids. In some embodiments of the invention, the amino acid sequence of the member of the Cecropin family comprises 25-130 amino acids. In some embodiments of the invention, the amino acid sequence of the member of the Cecropin family comprises 20-40 amino acids. In some embodiments of the invention, the amino acid sequence of the member of the Cecropin family comprises 25-30 amino acids. In some embodiments of the invention, the amino acid sequence of the member of the Cecropin family comprises 20-50 amino acids. In some embodiments of the invention, the amino acid sequence of the member of the Cecropin family comprises 15-50 amino acids. In some embodiments of the invention, the amino acid sequence of the member of the Cecropin family comprises 20-70 amino acids. In some embodiments of the invention, the amino acid sequence of the member of the Cecropin family comprises 20-100 amino acids. In some embodiments of the invention, the peptide comprises a C-terminus group and/or an N terminus group wherein the C-terminus group and/or the N terminus group comprises one or more of cysteine, cysteine derivative, an amino acid sequence which contains cysteine or a group comprising a thiol moiety or any combination thereof.

In some embodiments of the invention, the c-terminus group and/or the N terminus group are each selected from the group consisting of cysteine, cysteine derivative, an amino acid sequence which contains cysteine or any other group comprising a thiol moiety. In some embodiments of the invention, the N-terminus group comprises the amino acid sequence methionine-cysteine, methionine-cysteine derivative, methionine derivative-cysteine or methionine derivative-cysteine derivative and the C-terminus group is cysteine or a cysteine derivative. In some embodiments of the invention, the C-terminus group comprises the amino acid sequence methionine-cysteine, methionine-cysteine derivative, methionine derivative-cysteine or methionine derivative-cysteine derivative and the N-terminus group is cysteine or a cysteine derivative.

In some embodiments of the invention, the N-terminus group and the C-terminus group are covalently bound so as to form a cyclic peptide. The covalent linkage may be a disulfide bond, an amide, lactam or peptide bond.

In some embodiments of the invention, the c-terminus group and the N terminus group are each selected from the group of L-amino acids, D-amino acids, non-natural amino acid or amino acid derivative.

In some embodiments of the invention, the peptide is self-assembled within a physiological membrane such that the intermolecular covalent linkage is formed between the N-terminus group of the peptide to the N-terminus or a C-terminus group of an additional identical peptide or wherein the intermolecular covalent linkage is formed between the C-terminus group of the peptide to the N-terminus or a C-terminus groups of an additional identical peptide.

In some embodiments of the invention, wherein the peptide is as set forth in SEQ ID Nos. 1-11. In some embodiments, the peptide is as set forth in SEQ ID. No. 6, which is also designated here OMN 6.

In some embodiments, the peptides of the invention are stabilized by an amide group added to the C-terminus group and or by an acetyl group to the N-terminus group. In some embodiments, the peptides of the invention are stabilized by any technique which is known in the art such as the addition of a non-proteinaceous or proteinaceous moiety.

In an embodiment of the invention, the non-proteinaceous is polyethylene glycol (PEG) or derivative thereof, polyvinyl pyrrolidone (PVP), albumin, divinyl ether, maleic anhydride copolymer (DIVEMA; and poly(styrene comaleic anhydride) (SMA), hyaluronic acid (HA), alginic acid (AA), polyhydroxyethyl methacrylate (Poly-HEMA), glyme or polyisopropylacrylamide or any combination thereof.

In one embodiment, this invention provides a functionally equivalent molecule that mimics the functional activity of any of the peptide or peptide variants provided in this invention. The term "functionally equivalent molecule" refers in the application to any compound such as but not restricted to peptidomimetic or stapled peptide. The functionally equivalent molecule may be obtained by retro-inverso or D-retro-enantiomer peptide technique, consisting of D-amino acids in the reversed sequence. The functionally equivalent molecule may be obtained by using amino acid derivative.

As used herein, in one embodiment, the term "amino acid derivative" refers to a group derivable from a naturally or non-naturally occurring amino acid, as described and exemplified herein Amino acid derivatives are apparent to those of skill in the art and include, but are not limited to, ester, amino alcohol, amino aldehyde, amino lactone, and N-methyl derivatives of naturally and non-naturally occurring amino acids. In an embodiment, an amino acid derivative is provided as a substituent of a compound described herein, wherein the substituent is —NH-G(Sc)—C(0)-Q or —OC(0)G(Sc)-Q, wherein Q is —SR, —NRR or alkoxyl, R is hydrogen or alkyl, Sc is a side chain of a naturally occurring or non-naturally occurring amino acid and G is C1-C2 alkyl. In certain embodiments, G is Ci alkyl and Sc is selected from the group consisting of hydrogen, alkyl, heteroalkyl, arylalkyl and heteroarylalkyl.

As used herein, in one embodiment, the term "peptide" may be derived from a natural biological source, synthesized, or produced by recombinant technology. It may be generated in any manner, including by chemical synthesis. One or more of the amino acids may be modified, for example, by the addition of a chemical entity such as a carbohydrate group, a phosphate group, a farnesyl group, an isofamesyt group, a fatty acid group, an acyl group (e.g., acetyl group), a linker for conjugation, functionalization, or other known protecting/blocking groups.

As used herein, in one embodiment, the term "peptide" may be fragments, derivatives, analogs, or variants of the foregoing peptides, and any combination thereof. "Fragments of peptides", as that term or phrase is used herein, include proteolytic fragments, as well as deletion fragments. "Variants of peptides" include fragments and peptides with altered amino acid sequences due to amino acid substitutions, deletions, or insertions.

Variants may occur naturally or be non-naturally occurring. Examples include fusion proteins, peptides having one or more residues chemically derivatized by reaction of a functional side group, and peptides that contain one or more naturally occurring amino acid derivatives of the twenty standard amino acids. These modifications may also include the incorporation of D-amino acids, or other non-encoded amino-acids. In one embodiment, none of the modifications should substantially interfere with the desired biological activity of the peptide, fragment thereof. In another embodiment, modifications may alter a characteristic of the peptide, fragment thereof, for instance stability or half-life, without interfering with the desired biological activity of the peptide, fragment thereof. In one embodiment, as used herein the terms "peptide" and "protein" may be used interchangeably having all the same meanings and qualities.

In one embodiment, peptides of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the peptide of the present invention and fused cleavable moiety. In one embodiment, a fusion protein can be designed so that the peptide can be readily isolated by affinity chromatography; e.g., by immobilization on a column specific for the cleavable moiety. In one embodiment, a cleavage site is engineered between the peptide and the cleavable moiety and the peptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the peptide of the present invention is retrieved in a substantially pure form.

In one embodiment, the phrase "substantially pure" refers to a purity that allows for the effective use of the protein in the applications described herein.

In one embodiment, the peptide of the present invention can also be synthesized using in vitro expression systems. In one embodiment, in vitro synthesis methods are well known in the art and the components of the system are commercially available.

In one embodiment, a peptide of this invention is produced ⏰ synthetic process. In some embodiments the peptide is produced using recombinant DNA technology. A "recombinant" peptide, or protein refers to a peptide, or protein produced by recombinant DNA techniques; i.e., produced from cells transformed by an exogenous DNA construct encoding the desired peptide or protein.

In some embodiments, the recombinant peptides, fragments thereof or peptides are synthesized and purified; their therapeutic efficacy can be assayed either in vivo or in vitro. In one embodiment, the activities of the peptides of the present invention can be ascertained using various assays including inter-alia cell viability, survival of mice, and recovery of wounds.

In one embodiment, a peptide of this invention comprises at least 20 amino acids. In another embodiment, a peptide comprises at least 25 amino acids. In other embodiments, a peptide comprises at least 30 amino acids or at least 50 amino acids or 75 amino acids, or 100 amino acids, or 125 amino acids, or 150 amino acids, or 200 amino acids, or 250 amino acids or 300 amino acids or 350 amino acids or 400 amino acids.

As used herein, in one embodiment, the terms "peptide" and "fragment" may be used interchangeably having all the same meanings and qualities. As used herein, in one embodiment the term "peptide" includes native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into bacterial cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided herein under.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several locations (2-3) at the same time.

Natural aromatic amino acids, Trp, Tyr and Phe, may be substituted for synthetic non-natural acids such as TIC, naphthylelanine (Nol), ring-methylated derivatives of Phe, halogenated derivatives of Phe or o-methyl-Tyr.

As used herein, in one embodiment the term "amino acid" refers to naturally occurring and synthetic α, β γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In certain embodiments, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. As used herein, in one embodiment the phrase "Conservatively modified variants" applies to both amino acid and nucleic acid sequences. "Amino acid variants" refers to amino acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations", which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant", including where the alteration results in the substitution of an amino acid with a chemically similar amino acid. Conservative substitution tables providing functionally similar amino acids are well known in the art. Guidance concerning which amino acid changes are likely to be phenotypically silent can also be found in Bowie et al., 1990, Science 247: 1306 1310. Such conservatively modified variants are in addition to and do not exclude polymorphic variants, interspecies homologs, and alleles. Typical conservative substitutions include but are not limited to: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)) Amino acids can be substituted based upon properties associated with side chains, for example, amino acids with polar side chains may be substituted, for example, Serine (S) and Threonine (T); amino acids based on the electrical charge of a side chains, for example, Arginine (R) and Histidine (H); and amino acids that have hydrophobic side chains, for example, Valine (V) and Leucine (L). As indicated, changes are typically of a minor nature, such as conservative amino acid substitutions that do not significantly affect the folding or activity of the protein.

In some embodiments, the peptide of the invention is an isolated peptide. As used herein, in one embodiment the term "isolated" means altered "by the hand of man" from its natural state; i.e., that, if it occurs in nature, it has been changed or removed from its original environment, or both.

The peptides of the invention may be assayed for example by an agarose dilution MIC assay, a broth dilution, time-kill assay, or equivalent methods. Antibiotic activity is measured as inhibition of growth or killing of a microorganism (e.g., bacteria, fungi).

According to another embodiment of the invention, under oxidative environment, e.g. as in infections, the cysteines in the carboxy- and amino-terminus of the peptide of the invention are covalently attached to one another, thus creating in some embodiments, a cyclic form of the peptide, which represents higher stability while maintaining the peptide's original biological activity or even an improved activity compared to the original form. In some embodiments, these peptides are used as an antibiotic medicament.

The invention also provides a method for expressing the novel cysteine harboring peptides from the Cecropin family in single cell heterologous expression systems. The method enables a large scale expression while avoiding rapid degradation by proteolysis activity.

According to some embodiments of the invention, there is provided a nucleic acid sequence encoding the peptide of any one of the sequences as set for in SEQ ID Nos. 1-11 or a vector comprising the nucleic acid sequence encoding the peptide of any one of the sequences as set for in SEQ ID Nos. 1-11.

A massive production of AMCP's in heterologous expression system such as the yeast strains *Saccharomyces cerevisiae/Pichia pastoris* or compatible bacteria strains, serves in some embodiments of the invention to generate a 1 class of agents effective against a wide range of both Gram-positive and Gram-negative bacteria which overcome the problem of antibiotic resistance.

According to one method of the invention, the desired genes, such as, but not limited to, any of the peptides listed in Table 1, e.g. the AMCP6 gene (SEQ ID NO:25), are identified, isolated, and cloned into a suitable vector after the addition of Cysteine codons to each of the carboxy- and amino-terminus of the genes. The vector is suitable for high-quantity expression of the target peptides, e.g. pPIC9K and pET28 plasmids, and are transformed into an acceptable target expression system, e.g. BL21, *Pichia pastoris, Saccharomyces cerevisiae* cells, etc.

Desired genes encoding proteins from the Cecropin family are genetically engineered to possess an even number of cysteines located at their carboxy and amino terminus Table 1 provides a detailed list of several peptides of the Cecropin family, including their naive amino acid sequence and the added Cysteine and Methionine residues.

One method of the invention is the insertion of an ATG codon (encoding the methionine amino acid) to the 5' of mature Cecropin genes. When unmodified peptides are engineered and cysteine residues are inserted downstream of native ATG codon.

In another embodiment of the invention, the insertion of desired AMCP gene downstream to a region encoding for 6 histidine residues (His-Tag) is provided. A large number of compatible vectors suitable for this purpose are known to those of skill in the art. One example of the invention is the use of the vector pET28a, for the expression of the peptides in compatible bacterial expression system. The use the 6 histidine residues His-Tag is a well-known technique for isolation and purification of proteins from expression system cells.

The use of eukaryotic expression systems is commonly used for the production of foreign proteins. One example of such system is the methanoltrophic *Pichia pastoris* yeast strain. *P. pastoris* has been developed into an excellent host system for massive production of desired proteins. One of the advantages of using *P. pastoris* over *E. coli* bacterial cells is that the proteins of interest are usually folded correctly and secreted to the growth medium. Furthermore, *P. pastoris* does not have the endotoxin problem associated with bacteria especially when concerning antimicrobial peptides as required in this invention. Therefore, one embodiment of the invention is the insertion of AMCP genes into pPIC9K, a *Pichia* Vector for multi-copy integration and secreted expression (Invitrogen). AMCP gene of choice is cloned into said expression, resulting in pPIC9K-AMCP (9.5 Kb). Cloning the AMCP genes downstream to the AOX1 promoter verifies that their expression is under its regulation. For example, AMCP gene containing ATG-TGC codons, encoding methionine and cysteine respectively, at the 5' of its naïve origin; and TGC-codon, encoding cysteine, at its 3'; results in the expression of desired cyclic peptides of the invention.

According to some embodiment of the invention, there is provided a method of overcoming inherent or acquired resistance of a microorganism to an antibiotic agent, comprising: contacting the microorganism to the peptide of the invention as described herein. The microorganism is, in some embodiments, *Escherichia coli, Klebsiella Pneumoniaea, Pseudomonas aeruginosa, Salmonella* serotype *Typhi, Acinetobacter baumannii*, a member of Enterobacteriaceae spp., *Pseudomonas* spp. *Salmonella* spp., *Acinetobacter* spp. or any combination thereof, As used herein "inherent resistance" of a microorganism to an antibiotic agent refers to a natural resistance to the action of the agent even in the absence of prior exposure to the agent. (R. C. Moellering Jr., Principles of Anti-infective Therapy; In: Principles and Practice of Infectious Diseases, 4.sup.th Edition, Eds.; G. L. Mandell, J. E. Bennett, R. Dolin. Churchill Livingstone, N.Y. USA, 1995, page 200).

As used herein, "acquired resistance" of a microorganism to an antibiotic agent refers to a resistance that is not inhibited by the normal achievable serum concentrations of a recommended antibiotic agent based on the recommended dosage. (NCCLS guidelines).

As used herein, "tolerance" of a microorganism to an antibiotic agent refers to when there is microstatic, rather than microcidal effect of the agent. Tolerance is measured by an MBC:MIC ratio greater than or equal to 32. (Textbook of Diagnostic Microbiology, Eds., C. R. Mahon and G. Manuselis, W.B. Saunders Co., Toronto Canada, 1995, page 92).

As noted above, this invention provides methods of treating infections caused by a microorganism, methods of killing a microorganism, and methods of enhancing the activity of an antibiotic agent. In particular, these methods are especially applicable when a microorganism is resistant to an antibiotic agent, by a mechanism, such as tolerance, inherent resistance, or acquired resistance. In this invention, infections are treated by administering a therapeutically effective dose of a cationic peptide alone or in combination with an antibiotic agent to a patient with an infection. Similarly, the combination can be contacted with a microorganism to effect killing.

In some embodiments of the invention, there is provided a method of disinfecting a wound comprising contacting the wound with the peptide or the pharmaceutical composition of the invention. The wound may be in some embodiments, a blister wound, a soft tissue wound, a cutaneous abscess, a surgical wound, a sutured laceration, a contaminated laceration, a burn wound, a decubitus ulcer, a stasis ulcer, a leg ulcer, a foot ulcer, a venous ulcer, a diabetic ulcer, an ischemic ulcer, a pressure ulcer, an oral infection, a periodontal disease, a partial thickness burn, or a full thickness burn.

In some embodiments of the invention, there is provided a method of treating an infection, the method comprising administering the peptide or the pharmaceutical composition of the invention to a subject in need thereof.

In some embodiments of the invention, the invention provides use of the peptide as described herein or a pharmaceutical composition comprising the same in the preparation of a medicament for treating an infection in a subject. The infection may be bacterial, viral- and/or fungal infection.

As used herein in the specification and in the claims section below, the term "treat" or "treating" and their derivatives includes substantially inhibiting or slowing a pathogen growth, or killing the same. The pathogen may be selected from bacteria, virus, parasite and pathologic fungi.

According to a method of the invention, the peptide of the invention should be used in an effective amount to treat infections in mammals. As used herein, "effective amount" means an amount necessary to achieve the desired result. For example, an effective amount of the peptides of the invention to remove a bacterial infection from a mammal within 3 days, 4 days, 5 days, 7 days or 10 days. The "effective amount" for purposes herein is that determined by such considerations as are known in the art. Effective doses may be extrapolated from dose-response curves derived from in vitro or animal model test systems. It is to be understood that the "effective amount" is dependent on the treated bacteria, the subject's physical condition, etc. Determination of optimal ranges of effective amounts of the active ingredient, is within the skill of the art.

In some embodiments of the invention, there is provided a pharmaceutical composition comprising the peptide of the invention. The pharmaceutical composition may be in a form of a liquid, cream, gel, paste, powder, emulsion, an ointment, a liniment, a lotion, a transdermal system, an injection fluid, a suspension, a patch film patch or spray. In some embodiments, the formulation is in a form of capsule or a tablet or designed for being injected. The composition may be administered in conjunction with one or more additional anti-inflammatory active agent.

According to an embodiment, the compositions of the present invention may be formulated for topical, oral, ocular or pulmonary (e.g. for inhalation) administration. Other formulations are described hereinbelow and are within the scope of the invention.

As used herein a "pharmaceutical composition" refers to a preparation of the active ingredients described herein with other chemical components such as physiologically suitable carriers and excipients. The purpose of the composition is to facilitate administration of the active ingredients (e.g., the peptides of the invention) to the subject.

As used herein the term "active ingredient" refers to the peptide compositions accountable for the intended biological effect (i.e., for treatment or prevention of an infection).

Hereinafter, the phrases "physiologically acceptable carrier" and "pharmaceutically acceptable carrier" which may be interchangeably used to refer to a carrier or a diluent that does not cause significant irritation to the subject and does not abrogate the biological activity and properties of the administered active ingredients. An adjuvant is included under these phrases.

Herein, the term "excipient" refers to an inert substance added to the composition (pharmaceutical composition or cosmetic composition) to further facilitate administration of an active ingredient of the present invention.

Techniques for formulation and administration of drugs may be found in "Remington's Pharmaceutical Sciences" Mack Publishing Co., Easton, Pa., latest edition, which is incorporated herein by reference.

Techniques for formulation and administration may be found in "Remington: The Science and Practice of Pharmacy" Twentieth Edition, Lippincott Williams & Wilkins, Philadelphia, Pa. (1995). For human or animal administration, preparations should meet sterility, pyrogenicity, general safety and purity standards comparable to those required by the FDA. Administration of the pharmaceutical formulation can be performed in a variety of ways, as described herein.

Another aspect of the present invention relates to a pharmaceutical composition including a pharmaceutically acceptable carrier and an active ingredient which is the peptide of the invention. The phrase "active ingredient" refers to any of the peptides, the fragments thereof, the functionally equivalent molecule that mimics the functional activity of the peptide, or a polynucleotide encoding a peptide according to the embodiments of the present invention. The pharmaceutical composition can contain one or more of the above-identified active ingredients of the present invention. Typically, the pharmaceutical composition of the present invention will include an active ingredient of the present invention, as well as a pharmaceutically acceptable carrier. The term "pharmaceutically acceptable carrier" refers to any suitable adjuvants, carriers, excipients, or stabilizers, and can be in solid or liquid form such as, tablets, capsules, powders, solutions, suspensions, or emulsions.

Typically, the composition will contain from about 0.01 to 99 percent of the active ingredient. In some embodiments, the composition will contain from about 20 to 75 percent of an active ingredient and will further contain adjuvants, carriers and/or excipients. Determination of optimal ranges of effective amounts of the active ingredient is within the skill of the art. In some embodiments, the pharmaceutical composition may comprise about 0.01 to about 100 mg/kg body-weight of the peptide. In some embodiments, the pharmaceutical composition may comprise about 0.5 to about 100 mg/kg body-weight of the peptide. In some embodiments, the pharmaceutical composition may comprise about 100 to about 500 mg/kg body-weight of the peptide. In some embodiments, the pharmaceutical composition may comprise about 100 to about 300 mg/kg body-weight of the peptide. Treatment regimen for the administration of the peptide of the present invention can also be determined readily by those with ordinary skill in art. That is, the frequency of administration and size of the dose can be established by routine optimization.

In some embodiments, the pharmaceutical composition is in a form of a solid unit dosage form such as a capsule, tablet and the like, such as an ordinary gelatin type containing the active ingredient thereof of the present invention, and a carrier, for example, lubricants and inert fillers such as, lactose, sucrose, or cornstarch. In another embodiment, the active ingredient is tabulated with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate. The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, the active ingredient can be incorporated with excipients and used in the form of tablets, capsules, elixirs, suspensions, syrups, and the like.

The active ingredient of the present invention may be orally administered, for example, with an inert diluent, or with an assimilable edible carrier, or they can be enclosed in hard or soft shell capsules, or they can be compressed into tablets, or they can be incorporated directly with the food of the diet.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

For use as aerosols, the active ingredient thereof of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

When administering the active ingredient of the present invention, and pharmaceutical compositions thereof, they can be administered systemically or, alternatively, they can be administered directly to a specific site. Thus, administering can be accomplished in any manner effective for delivering the active ingredients thereof or the pharmaceutical compositions to the specific targeted cells. Exemplary modes of administration include, without limitation, administering the active ingredients thereof or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Toxicity and therapeutic efficacy of the peptides described herein can be determined by standard pharmaceutical procedures in cell cultures or experimental animals, e.g., by determining the IC50 (the concentration which provides 50% inhibition) and the LD50 (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See, for example, Fingl et al., 1975, in The Pharmacological Basis of Therapeutics, Ch. 1 p. 1, the contents of which are hereby incorporated by reference in their entirety).

Depending on the severity and responsiveness of the condition to be treated, dosing can also be a single administration of a slow release composition, with course of treatment lasting from several days to several weeks or until cure is effected or diminution of the disease state is achieved.

The amount of a composition to be administered will, of course, depend on the subject being treated, the severity of the affliction, the manner of administration, the judgment of the prescribing physician, and all other relevant factors. Determination of the exact dose to be administered is conducted by methods known to a person of skill in the art.

It is further understood that the active ingredient of the invention can be formulated or administered together with additional active ingredients as required to treat the condition of the patient.

Alternately, one may administer the composition in a local rather than systemic manner, for example, by injecting the composition including the active ingredient (and a physiologically acceptable carrier) directly into a tissue region of a patient (e.g. to the infected skin or into a healthy skin that surrounds the infected skin).

Suitable routes of administration of the compositions may, for example, include ocular (e.g., to the eye), topical (e.g., to a keratinous tissue, such as the skin, hair, nail, scalp), transdermal, subdermal, pulmonary and oral (e.g., by mouth) administrations.

According to an embodiment, the composition of the present invention is administered topically, pulmonary (e.g. via inhalation), orally or ocularly.

As used herein the phrase "dermal administration" refers to applying or spreading the composition of the present invention onto the surface of the body, i.e. skin, scalp, hair, nails and the like, preferably on the surface affected by the infection.

As used herein the phrase "transdermal administration" refers to administration of the compositions of the present invention across the skin for systemic administration (e.g. via transdermal patches or by transdermal implants). The transdermal administration is typically effected in close proximity to the site of infection, however, transdermal administration may be carried out in any anatomical location as see fit by one of ordinary skill in the art.

As used herein the phrase "subdermal administration" refers to administering the compositions of the present invention under the skin (i.e. completely buried in the skin, e.g. via subdermal implants). The subdermal administration is typically effected in close proximity to the site of the infection, however, subdermal administration may be carried out in any anatomical location as see fit by one of ordinary skill in the art.

Compositions of the present invention may be manufactured by processes well known in the art, e.g., by means of conventional mixing, dissolving, granulating, dragee-making, levigating, emulsifying, encapsulating, entrapping or lyophilizing processes.

Compositions for use in accordance with some embodiments of the invention thus may be formulated in conventional manner using one or more physiologically acceptable carriers comprising excipients and auxiliaries, which facilitate processing of the active ingredients into preparations which, can be used cosmetically or pharmaceutically. Proper formulation is dependent upon the route of administration chosen.

In addition, a dose can be formulated in tissue cultures systems (e.g. ex-vivo systems) or in animal models to achieve a desired concentration or titer. Such information can be used to more accurately determine useful doses in humans. For example, a therapeutically effective amount can be evaluated in-vivo by determining the level of inflammation before and after administration of the composition in a subject affected by an inflammatory state [e.g. by use of a blood test such as a complete blood count (CBC), by observation of skin wounds and so forth].

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in humans. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Depending on the severity of the condition (e.g., the area, depth and degree of the infection) and the responsiveness of the subject to treatment, dosing can be of a single or a plurality of administrations, with course of treatment lasting from several days to several weeks, several months or several years, or until cure is effected or diminution of the infection is achieved. Alternatively, the compositions are administered in order to prevent occurrence of an infection in a subject at risk of developing an infection (e.g. a subject suffering from a chronic inflammatory disease). The compositions may be administered for prolonged periods of time (e.g. several days, several weeks, several months or several years) as to prevent occurrence of an infection.

According to an embodiment of the present invention, the compositions of the present invention are administered at least once a day. According to another embodiment, the compositions are administered twice a day, three times a day or more.

According to an embodiment of the present invention, administering is effected chronically.

According to another embodiment, administering is effected for at least about 10 days, 12 days, 14 days, 16 days, 18 days, 21 days, 24 days, 27 days, 30 days, 60 days, 90 days or more.

The amount of a composition to be administered will, of course, be dependent on the subject being treated, the severity of the affliction, the manner of administration, the judgment of the prescribing physician, etc.

The compositions of the present invention may be formulated as a unit dosage form. In such form, the preparation is subdivided into unit doses containing appropriate quantities of the active ingredients such as for a single administration. The unit dosage form can be a packaged preparation, the package containing discrete quantities of preparation, for example, an ampule, a dispenser, an adhesive bandage, a non-adhesive bandage, a wipe, a baby wipe, a gauze, a pad and a sanitary pad.

Additional factors may be incorporated into the compositions of the present invention (i.e., plant extracts as described hereinabove). These include, but are not limited to, extracellular matrix components (e.g. vitronectin, laminin, collagen, elastin), growth factors (e.g. FGF 1, FGF 2, IGF 1, IGF 2, PDGF, EGF, KGF, HGF, VEGF, SDF-1, GM-CSF, CSF, G-CSF, TGF alpha, TGF beta, NGF and ECGF), growth factors [e.g. erythropoietin, fibroblast growth factor, franulocyte-colony stimulating factor (G-CSF) and granulocyte-macrophage colony stimulating factor (GM-CSF)], hormones (e.g., insulin, growth hormone (GH), CRH, Leptin, Prolactin and TSH), angiogenic factors (e.g., angiogenin and angiopoietin), coagulation and anticoagulation factors [e.g., Factor I, Factor XIII, tissue factor, calcium, vWF, protein C, protein S, protein Z, fibronectin, antithrombin, heparin, plasminogen, low molecular weight heparin (Clixan), high molecular weight kininogen (HMWK), prekallikrein, plasminogen activator inhibitor-1 (PAI1), plasminogen activator inhibitor-2 (PAI2), urokinase, thrombomoduline, tissue plasminogen activator (tPA), alpha 2-antiplasmin and Protein Z-related protease inhibitor (ZPI)], cytokine inhibitors (e.g. Cyclosporin A; Alpha-2-Macroglobulin, Pentamidine, Pentoxifylline, Dexamethasone), chemokine inhibitors (e.g. Peptide 3, NR58.3-14-3), enzymes (e.g. endoglycosidases, exoglycosidases, endonucleases, exonucleases, peptidases, lipases, oxidases, decarboxylases, hydrases, chondroitinase, chondroitinase ABC, chondroitinase AC, hyaluronidase, keratanase, heparanases, heparanase splice variance, collagenase, trypsin, catalases), neurotransmitters, neuropeptides (e.g. substance P), vitamins (e.g., D-biotin, Choline Chloride, Folic acid, Myo-inositol, Niacinamide, D-Pantothenic acid, Calcium salts, Pyridoxal.HCl, Pyrodixine.HCl, Riboflavin, Thiamine HCl, Vitamin B12, vitamin E, vitamin C, vitamin D, vitamin B1-6, vitamin K, vitamin A and vitamin PP), carbohydrates (e.g. Mono/Di/Polysacharides including glucose, mannose, maltose and fructose), ions, chelators (e.g. Fe chelators, Ca chelators), antioxidants (e.g., Vitamin E, Quarcetin, superoxide scavengers, Superoxide dismutase, H2O2 scavengers, free radicals scavengers, Fe scavengers), fatty acids (e.g., Triglycerides, Phospholipids, Cholesterols, free fatty acids and non free fatty acids, fatty alcohol, Linoleic acid, oleic acid and lipoic acid), antibiotics (e.g., Penicillins, Cephalosporins and Tetracyclines), amino acids (e.g., essential and non essential (from A-Z) especially glutamine and arginine), salts (e.g., pruruvat salts and sulfate salts), sulfates (e.g. Calcium Sulfate), steroids (e.g., androgens, estrogens, progestagens, glucocorticoids and mineralocorticoids), analgesics, anesthetics, anti-bacterial agents, anti-yeast agents, anti-fungal agents, anti-viral agents, pro-biotic agents, antiprotozal agents, anti-pruritic agents, anti-dermatitis agents, anti-emetics, anti-inflammatory agents, anti-hyperkeratolyic agents, antiperspirants, anti-seborrheic agents, antihistamine agents, hypoxia inducible factors (e.g. HIF-1 alpha and beta and HIF-2), catecholamines (e.g., Epinephrine and Norepinephrine), Nucleosides and Nucleotides (e.g., Purins and Pyrimidines), Prostaglandins (e.g. Prostaglandin E2), Leucotriens, Erythropoietins (e.g. Thrombopoietin), Proteoglycans (e.g. Heparan sulfate, keratan sulfate), Hydroxyapatites [e.g. Hydroxyapatite (Ca10(PO4)6(OH)2)], Haptoglobins (Hp1-1, Hp2-2 and Hp1-2), Superoxide dismutases (e.g. SOD 1/2/3), Nitric Oxides, Nitric Oxide donors (e.g. nitroprusside, Sigma Aldrich, St. Louis, Mo., USA, Glutathione peroxidases, Hydrating compounds (e.g. vasopressin), cells (e.g. Platelets), cell medium (e.g. M199, DMEM/F12, RPMI, Iscovs), serum (e.g. human serum, fetal calf serum, fetal bovine serum), buffers (e.g., HEPES, Sodium Bicarbonate), detergents (e.g., Tween), disinfectants, herbs, fruit extracts, vegetable extracts (e.g. cabbage, cucumber), flower extracts, additional plant extracts, flavinoids (e.g. pomegranate juice), spices, leafs (e.g. Green tea, Chamomile), Polyphenols (e.g. Red Wine), honey, lectins, microparticles, nanoparticles (lyposomes), micelles, calcium carbonate (CaCO3, e.g. precipitated calcium carbonate, ground/pulverized calcium carbonate, albacar, PCC, GCC), calcite, limestone, crushed marble, ground limestone, lime, and chalk (e.g. whiting chalk, champagne chalk, french chalk).

The present formulation may also contain ingredients, substances, elements and materials containing, hydrogen, alkyl groups, aryl groups, halo groups, hydroxy groups, alkoxy groups, alkylamino groups, dialkylamino groups, acyl groups, carboxyl groups, carboamido groups, sulfonamide groups, aminoacyl groups, amide groups, amine groups, nitro groups, organo selenium compounds, hydrocarbons, and cyclic hydrocarbons.

The present formulation may be combined with substances such as benzol peroxide, vasoconstrictors, vasodilatators, salicylic acid, retinoic acid, azelaic acid, lactic acid, glycolic acid, pyreuric acid, tannins, benzlidenecamphor and derivatives thereof, alpha hydroxyis, surfactants.

Compositions of some embodiments of the present invention may be bioconjugated to polyethylenglycol (e.g. PEG, SE-PEG) which preserves the stability (e.g., against protease activities) and/or solubility (e.g., within a biological fluid such as blood, digestive fluid) of the active ingredients (i.e. plant extract compositions of the present invention) while preserving their biological activity and prolonging its half-life.

The carrier utilized in the compositions of the invention can be in a wide variety of forms. These include emulsion carriers, including, but not limited to, oil-in-water, water-in-oil, water-in-oil-in-water, and oil-in-water-in-silicone emulsions, a cream, an ointment, an aqueous solution, a lotion, a soap, a paste, an emulsion, a gel, a spray or an aerosol.

Methods for preparing compositions having such properties are well known to those skilled in the art, and are described in detail in Remington's Pharmaceutical Sciences, 1990 (supra); and Pharmaceutical Dosage Forms and Drug Delivery Systems, 6th ed., Williams & Wilkins (1995).

EXAMPLES

Example 1

Enhanced Stability of OMN6 in Comparison with Native Cecropin A and BSA

Figure 1A:
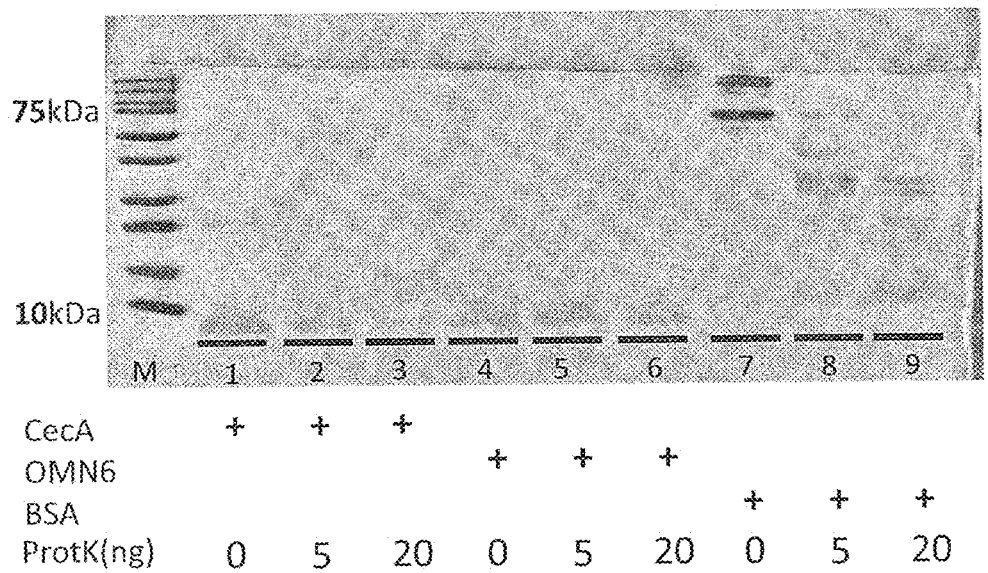
FIG. 1A depicts a Coommassie Blue (Brilliant Blue R, Sigma Chemical Company, USA) stained gel detecting the following: Lanes 1-3: Native Cecropin-A (CecA) subjected to Proteinase-K (ProtK) proteolysis in increasing concentrations: 0/5/20 ng/30 µl as mentioned. Lanes 4-6: OMN6 subjected to ProtK proteolysis in increasing concentrations: 0/5/20 ng/30 µl as mentioned. Lanes 7-9: Bovine Serum Albumin (BSA) subjected to ProtK proteolysis in increasing concentrations: 0/5/20 ng/30 µl as mentioned. Proteolysis of CecA and BSA resulted in the disappearing of the band from the gel. Proteolytic activity of ProtK did not affect OMN6 and all the bands were present.
Figure 1B:
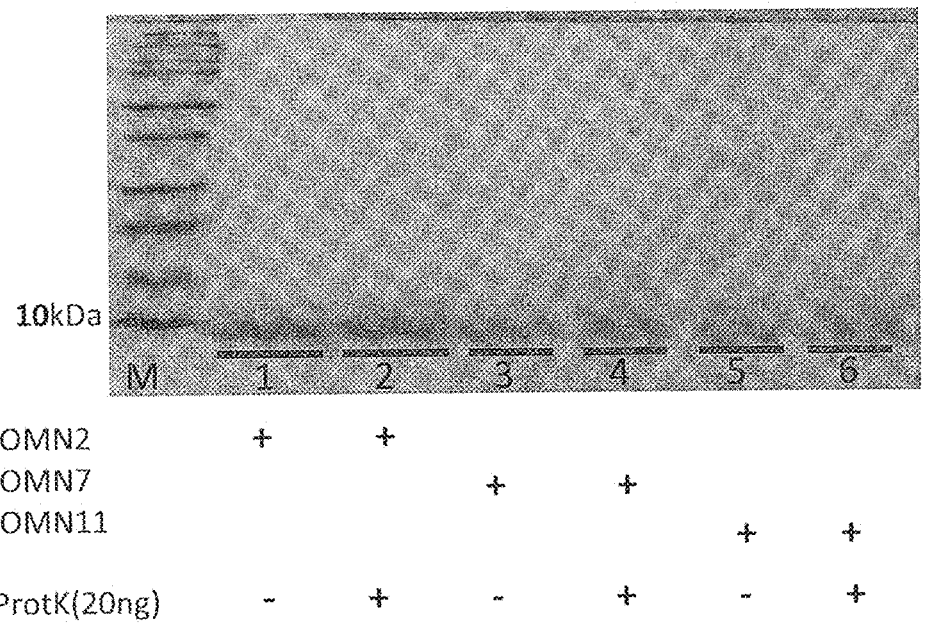
FIG. 1B depicts Coommassie blue stained gel detecting the stability of peptides OMN2, OMN7 and OMN11 against ProtK activity. The stability of each peptide with or without incubation with ProtK was presented (right lane and left lane, respectively). Clearly, peptides OMN2, OMN7 and OMN11 were not degraded by the depredating activity of ProtK. The bands are of the same intensity either for the ProtK treated peptide as for the non-treated peptide, namely, ProtK had no depredating effect on these peptides.

Proteinase-K (ProtK) was used to assess the stability of OMN6 versus native Cecropin A (CecA) and Bovine Serum Albumin (BSA) (See FIG. 1 A). 10 µg of each protein were incubated with increasing concentrations of between 5-20 ng of ProtK as specified, for 2 hours at 37° C. Samples were boiled at 100° C. for five minutes and separated on 15% acrylamide gel. The gel was then stained with Coommassie Blue and excess dye was removed over-night. Results clearly show that 20 ng of ProtK was sufficient to completely degrade CecA and BSA (lanes: 3, 9 respectively). As can be seen, OMN6 is protected from ProtK proteolysis and was not degraded (lane: 6). Results also show that ProtK at a low concentration of 5 ng was sufficient to partially degrade CecA and BSA (lanes: 2, 8 respectively). In lane 2, the CecA band was weaker than the untreated sample band in lane 1. In lane 8, fragments of degraded BSA were detected, evidence of partial degradation. OMN6 was not degraded by ProtK at all. These results prove that OMN6, after the genetic engineering, is more stable than its native form, Cecropin A. The same experimental system as described above was used to assess the stability of OMN2, OMN7 and OMN11 against proteolytic degradation by ProtK (see FIG. 1B). In each case, as specified, results show that OMN peptides are not degraded by ProtK. The peptides are stable as can be seen from the equal intensity of the bands presented for each peptide.

Example 2

Figure 2A:
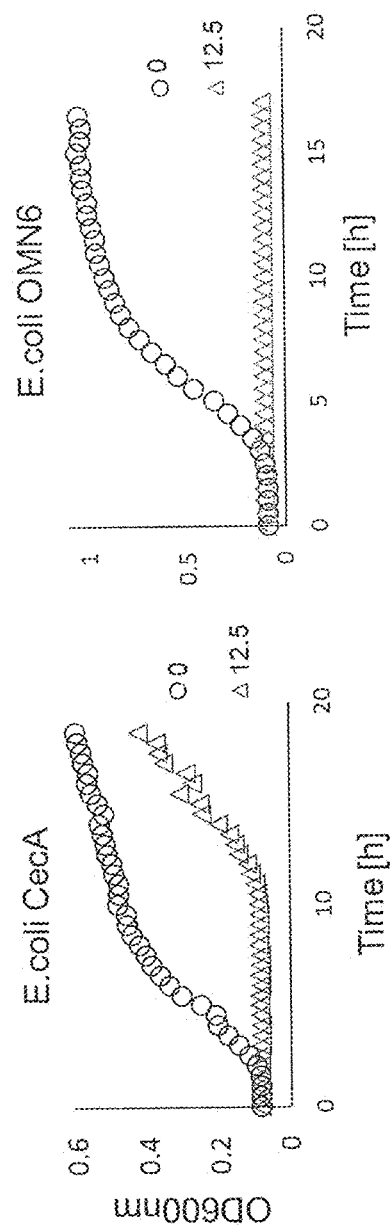
FIG. 2A: Right graph demonstrates *E. coli* bacteria growth monitored over 17.5 hours via absorbance at 600 nm. Bacteria growth or inhibition of growth is presented as OD600 nm values over time. As the bacteria grow, OD values increase. OMN6 antimicrobial effect is demonstrated by the decreased OD values that represent bacterial death in the presence of OMN6. Left graph same experiment as described above was conducted with *E. coli* bacteria and the native peptide Cecropin A (CecA). As is clearly seen after 10 hours CecA loses its antimicrobial activity and becomes ineffective. At that point, the bacteria overcome the growth inhibition and begin to grow and flourish. At the end of the experiment, bacteria treated with CecA reach the density and growth levels similar to that of the CTRL group (treated with DDW). These results strongly point to the fact that OMN6 is a stronger antimicrobial agent than CecA.

FIG. 2A: OMN6 Exerts a More Powerful Antimicrobial Effect than Native Peptide Cecropin-A An assay was conducted in order to compare the antimicrobial activity of the native peptide Cecropin A (CecA) vs. a peptide of the invention OMN6. E. coli bacteria were cultured with CecA or OMN6 in concentration of 12.5 µM for 17-20 hours. The growth of the bacteria was continuously monitored via spectrophotometry at 600 nm. As bacterial growth progresses, OD600 nm values rise, and where the growth is inhibited OD600 nm values remain constant. The results clearly show that at the concentration of 12.5 µM, the genetically engineered peptide OMN6 exerted a strong antimicrobial effect and completely inhibited bacterial growth for more than 17 hours, the entire duration of the experiment. At higher concentrations the bacterial growth was totally inhibited as well (data not shown). In contrast, when bacteria were incubated under the same experimental conditions with CecA at 12.5 µM, there was no significant inhibition of growth. The bacteria completely overcame the inhibitory effect of CecA after 10 hours. The bacteria then continued to thrive and grow to density similar to that of the CTRL group. These results taken together serve to strongly suggest that OMN6 is a new and stronger antimicrobial agent than its native counterpart CecA.

Figure 2B:
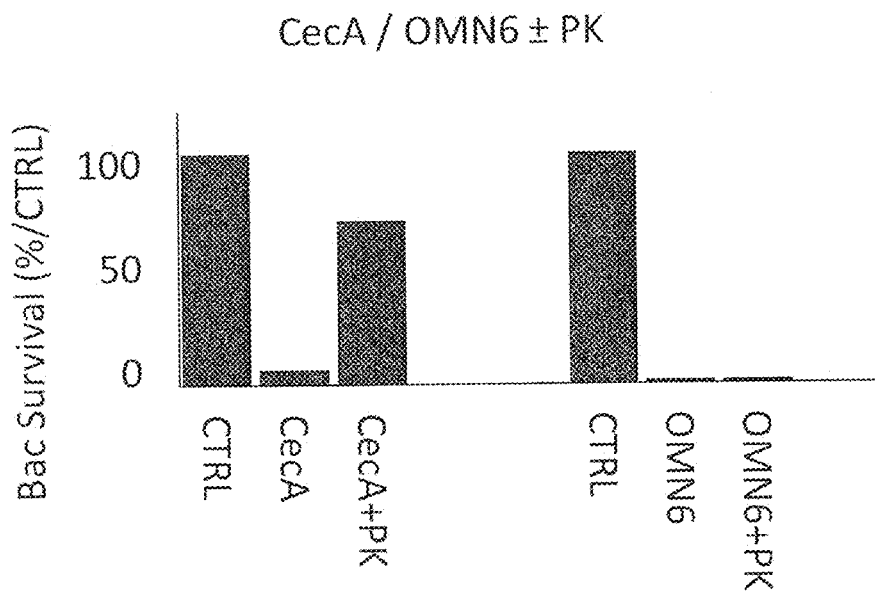
FIG. 2B depicts bacterial survival as percent survival of the control group (%/CTRL) in presence of CecA or one of the peptides of the invention, OMN6. Left Bars demonstrate bacterial survival in the presence of 12.5 µM of CecA pre-treated with 20 ng of ProtK. Right Bars demonstrate bacterial survival in the presence of 12.5 µM of OMN6 pre-treated with 20 ng of ProtK. CecA is degraded by ProtK therefore the bacteria survival is more than 70% of the CTRL group. OMN6 is stable and active, and accordingly the bacteria growth is inhibited to less than 10% of the CTRL group.

FIG. 2B: OMN6 is Stable in Presence of Proteinase-K and Retains its Potent Antimicrobial Activity The susceptibility of OMN6/CecA to proteolytic degradation was assessed and the effects of stability on activity were determined Native peptide-CecA and engineered peptide-OMN6 were incubated with 20 ng of Proteinase-K (ProtK) at 37° C. for two hours (left bars and right bars, respectively). E. coli at 500,000 CFU/ml were incubated for 18 hours with either CecA or OMN6 pretreated with ProtK. After the incubation, bacterial survival was determined via absorption at OD600 nm and via CFU count on agar plates.

The results as shown in FIG. 2A show that the genetically engineered peptide, OMN6, is a stronger antimicrobial agent than the native form CecA. The inhibition of bacterial growth exerted by CecA is overcome after 10 hours while OMN6 inhibits growth for more than 17 hours. Moreover, the effect of OMN6 is of a bactericidal nature as there were no colonies present when the experiment groups detailed in this example were plated. Most importantly, CecA is prone to proteolysis by ProtK and loses its antibacterial activity due to this degradation. It is clear that CecA treated with ProtK for 2 hours has lost its ability to kill bacteria. At 12.5 µM of CecA, bacteria are able to grow to more than 70% of the CTRL-control (non-treated bacteria group) (left bars). When OMN6 was treated with 20 ng of ProtK OMN6 was not degraded; rather, was stable and did not lose its antibacterial activity. At 12.5 µM of OMN6, bacteria growth was inhibited to less than 10% of the CTRL group (right bars).

Examples 1 and 2 emphasize that OMN6 is a stable peptide. OMN6 is a potent antimicrobial agent even after incubation with a strong protease like ProtK. In contrast, the native peptide CecA, which is prone to proteolysis, degrades by proteases and loses its ability to inhibit growth or kill bacteria after incubation with ProtK.

Example 3

OMN6 Treatment Leads to Bacteria Cell Lysis and Leakage of GFP from Cells to the Surrounding Media In order to determine and evaluate the Mechanism of Action (MOA) by which the peptides achieve the remarkable antimicrobial effect they exert, the following experiments were conducted: GFPuv *E. coli* bacteria are a strain that upon induction expresses green fluorescent protein (GFP). The GFP fluorescence can be detected at 395/509 nm, while live bacteria can be detected via absorbance at 600 nm (OD600).

Figure 3A:
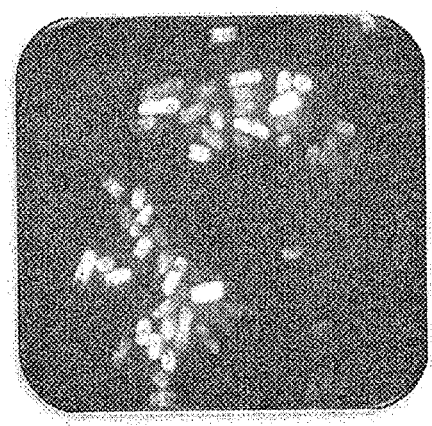
FIG. 3A shows bacteria treated with DDW as a control (CTRL). As can be seen the bacteria are alive, well defined, intact and GFP fluorescence is detected only inside the bacteria.
Figure 3B:
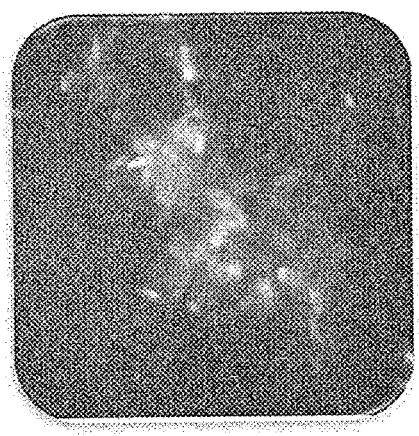
FIG. 3B shows bacteria treated with OMN6. The bacteria are dead, and have undergone extensive lysis, which allowed the GFP fluorescence to be detected outside of bacteria cells, in the surrounding media.

GFPuv *E. coli* bacteria ubiquitously express GFP in their cytoplasm upon induction and the fluorescent protein can be detected and visualized. The bacteria were grown and induced to express GFP for three hours, the bacteria were then treated with double distilled water (DDW) or OMN6 and incubated for 30 minutes (FIG. 3A, and FIG. 3B, respectively). At that point, the bacteria were imaged via a microscope (×60 Olympus lens) under UV light. In the CTRL group, treated with DDW, the bacteria were clearly unharmed. All the bacteria were alive, intact and there was no evidence of GFP leaking from inside the cells to the outside media (FIG. 3 A). When the *E. coli* GFPuv bacteria were treated with 50 μM OMN6 50 for 30 minutes, there was massive leaking of GFP from the cells' cytoplasm to the outside media (FIG. 3 B). Since GFP is a protein of 238 amino-acid residues (26.9 kDa), this protein is a large protein and it cannot leak from the cells when the plasma membrane is intact. It is evident that OMN6 punctures the membrane and leads to the formation of pores through which GFP can leak. The formation of these pores constitutes a physical damage that leads to the bacteria death. In contrast to small-molecule antibiotics, bacteria do not develop resistance against physical disturbance of pore formation in their plasma membrane.

Figure 4A:
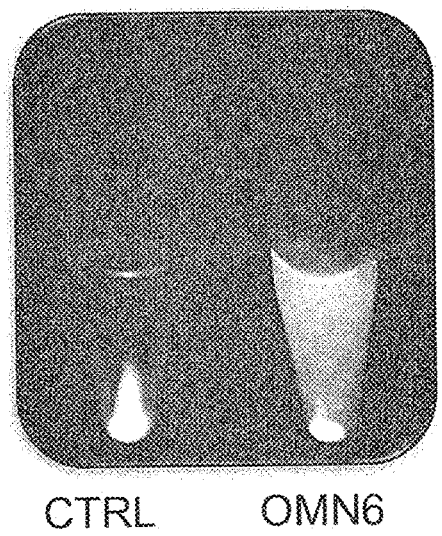
FIG. 4A Left Panel is a photograph showing the leaking of GFP from lysed bacteria to the surrounding media, after centrifugation with or without a treatment with OMN6. Bacteria in the left tube, receiving DDW sham treatment are alive, intact and all GFP fluorescence is limited to bacteria cells in pellet. Bacteria in right tube, receiving treatment with OMN6, have undergone extensive lysis and GFP fluorescence is clearly visible outside of dead bacterial cells and in the surrounding media.
Figure 4B:
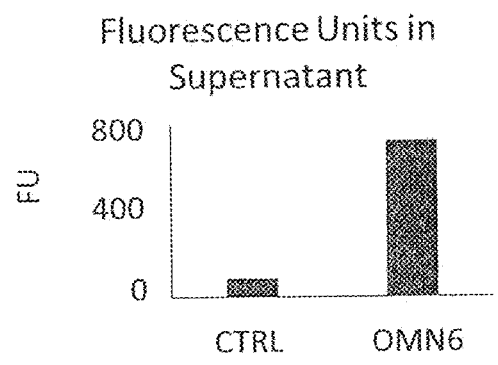
FIG. 4B demonstrates the graphical quantitation of the Fluorescence Units (FU) in each group.
Figures 5A, 5B, 5C, 5D:
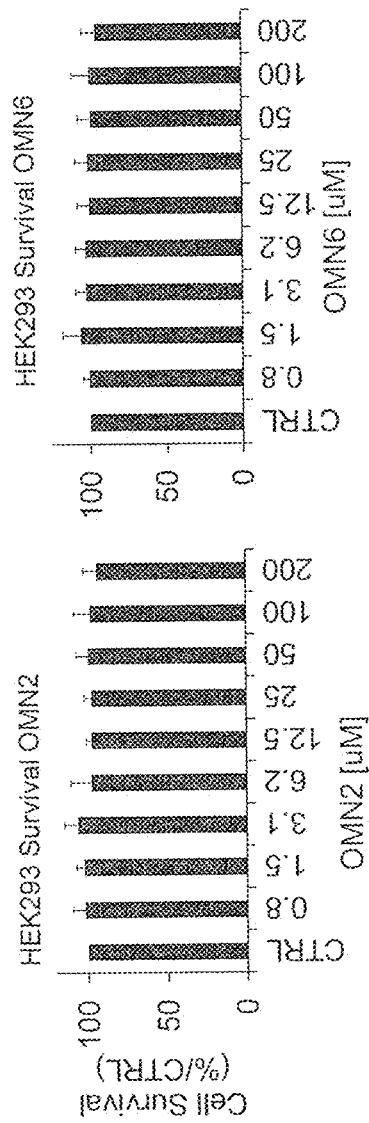
FIG. 5: presents the survival of HEK293 cells quantified via Methylene-Blue assay and presented as percent survival of CTRL (%/CTRL). A 24 hours treatment with increasing concentration of OMN2 (FIG. 5A), OMN6 (FIG. 5B), OMN7 (FIG. 5D) and OMN11 (FIG. 5C) does not lead to cell death or alteration of the survival fraction.

In another experiment, bacteria were grown and induced to express GFP. The bacteria were treated with DDW (for CTRL) or with OMN6. Bacteria were then centrifuged (5000 RPM for five minutes) and the pellet was separated from the growth media supernatant (see FIG. 4A). The supernatant (sup) from the two experiment groups CTRL and OMN6, was separated from the pellet and analyzed for the level of fluorescence units (FU) (see FIG. 4B). The results clearly show that in the CTRL group, where the bacteria remain unharmed, the intact bacterial cells retain all of the GFP. Fluorescence was detected only inside the bacteria which were concentrated in the pellet at the bottom of the tube. In the group treated with OMN6 50 μM for 30 minutes, the bacteria have undergone extensive lysis and as a result, GFP leaked out of the cells and was therefore found in the surrounding media. Both supernatants were probed for the presence of bacteria via absorbance at 600 nm and both supernatants were completely void of bacteria cells (data not shown). The rationale behind this experiment is that once the sup is free of bacteria cells, if the peptide causes the lysis of bacterial cells it will cause the GFP to leak out of the cells into the growth media. Thus, in the CTRL group, where the bacteria are intact, no fluorescence is detected in the sup while in the sup from the group treated with OMN6, the GFP that leaked out of the lysed cells is detected.

Example 4

OMN2, OMN6, OMN7 and OMN11 do not Present Cytotoxic Effects on HEK293 Cells

Human Embryonic Kidney 293 cells (HEK293) are human originated cells widely accepted as a model cell-line for evaluating adverse effects of potentially hazardous substances. HEK293 cells were cultured to 80% confluency and introduced to increasing concentrations of OMN2, OMN6, OMN7 and OMN11. CTRL group treated with DDW.

After 24 hours, all experiment groups were subjected to Methylene-Blue assay in-order to evaluate and determine cell survival. No significant changes in cell morphology or survival were observed in all of the groups (FIG. 5A-D).

Example 5

OMN6 does not Present Cytotoxic Effects on Human Primary Erythrocytes

Since the peptides of the invention are intended inter-alia to operate in wounds or other damaged tissue, a direct contact with patients' blood may occur. Accordingly, an experiment was conducted in order to assess whether OMN6 has cytotoxic effects on human primary erythrocytes. These cells lack any defense mechanism to protect them against damage to the plasma membrane and therefor are a standard model for evaluating cytotoxic effects on eukaryotic cells. The parameter that was measured was the ability of OMN6 to cause hemolysis, red blood cells death, in human erythrocytes. The experiments were performed on human blood samples using ABX PENTRA DF120 machine routinely used by hospital personnel to conduct such tests. The results show, that hemolysis of cells did not occur. The erythrocytes did not die as a result of being contact with OMN6. The number of cells at the beginning of the experiment has not been changed throughout the entire duration of the experiment in any of the experiment groups and the number of cells/mml did not vary between the CTRL group and the experiment group (Table 4).

The Mean Corpuscular Volume (MCV) of the erythrocytes is a well-accepted indication of the cells' health and membrane integrity. The experiment was conducted to assess whether OMN6, which forms pores in bacterial membranes, has the ability to damage human cells plasma-membrane. As can be seen from the results demonstrated in Table 5, OMN6 did not cause any decrease in cell volume throughout the time of the experiment. These results strongly indicate that the peptide does not damage eukaryotic cell-membranes. (Table 5).

OMN6 peptide does not target human membranes of primary erythrocytes and HEK293 cells. No significant reduction in cell counts or other adverse effect were observed with any of the peptides. These results show the peptides safety and their highly selective targeting of bacteria cells.

Table 4 and Table 5: hemolysis and Mean Corpuscular Values (MCV) of human primary erythrocytes were evaluated after treatment with OMN6. Treatment with OMN6 did not cause hemolysis of erythrocytes. Cell count was conducted and the number of cells/ml did not vary between CTRL group and experiment groups throughout the entire duration of the experiment (Table 4). Erythrocytes Mean Corpuscular Volume (MCV) was determined as well, MCV values did not change throughout the entire duration of the experiment and MCV values of experiment group did not vary from those of CTRL group (Table 5).

TABLE 4

Number of live erythrocytes (cells * $10^6$/ml)

| OMN6 [μM] | Time (min) | | | |
|---|---|---|---|---|
| | 30 | 60 | 120 | 180 |
| 0 | 1.67 | 1.68 | 1.65 | 1.66 |
| 10 | 1.69 | 1.66 | 1.68 | 1.67 |
| 20 | 1.65 | 1.70 | 1.71 | 1.70 |
| 40 | 1.60 | 1.80 | 1.77 | 1.76 |

TABLE 5

Erythrocytes Mean Corpuscular Volume (MCV)

| OMN6 [μM] | Time(min) | | | |
|---|---|---|---|---|
| | 30 | 60 | 120 | 180 |
| 0 | 65 | 64 | 63 | 64[10] |
| 10 | 64 | 64 | 63 | 64 |
| 20 | 64 | 64 | 63 | 64 |
| 40 | 64 | 64 | 63 | 64 |

Example 6

OMN Peptides Minimal Inhibitory Concentration (MIC) Values on Sensitive and Resistant Bacteria In-Vitro In order to determine the MIC values of the peptides, growth and inhibition of various bacteria were monitored after treatment with the peptides of the invention (Table 6). E. coli bacteria were cultured with or without OMN6 in increasing concentrations of 0.8-200 μM and with or without Fetal Bovine Serum 10% for 17-20 hours. The growth of the bacteria was continuously monitored via spectrophotometry at 600 nm. As bacterial growth progresses, OD600 nm values rise, and where the growth is inhibited OD600 nm values remain constant.

The results clearly show that at Minimal Inhibitory Conc. (MIC) of 12.5 μM, the genetically engineered peptide OMN6 exerted a strong antimicrobial effect and inhibited bacterial growth for 17 hours, at higher concentrations the bacterial growth was totally inhibited as well. When culture media is supplemented with FBS 10%, MIC value of OMN6 stands at 6.25 μM (FIG. 6B).

E. coli NDM1 is a Carbapenem resistant strain of bacteria. The experimental system described above was used to determine the antimicrobial effect of OMN6 on this bacteria compared to the antibiotic drug Imipenem (IPM), a member of the Carbapenem family of antibiotics. The MIC value for IPM on sensitive E. coli is 4 μg/ml, in a MIC above 8 μg/ml the bacteria is considered resistant. FIG. 6C clearly shows that even when the concentration of IPM is increased to 64 μg/ml, 16 times the value of MIC, the growth of the resistant bacteria is not inhibited at all. Moreover, this strain was also exposed to 128 μg/ml and growth was not inhibited at all (data not shown). When OMN6 12.5 μM was introduced to the system, it completely inhibited bacterial growth (FIG. 6D).

These results demonstrate that when bacteria develop resistance to a specific drug, this drug is no longer effective even at high concentrations. This drug can no longer be used for therapeutic purposes as it has lost its ability to kill the resistant bacteria. The bacteria resistance against a specific antibiotic drug or against a multitude of antibiotic drugs does not affect their susceptibility to the antimicrobial peptides of the invention.

The experimental system and parameters described here were used to determine the MIC values of OMN2, OMN6, OMN7 and OMN11 on various bacteria strains (Table 7 and Table 8).

TABLE 6

Bacteria Strains

| ATCC# | Resistance |
|---|---|
| Escherichia coli | NDM1 |
| ATCC ® BAA-2452 ™ | Carbepenem-resistant |
| | (Imipenem and Ertapenem) |
| Escherichia coli | ESBL |
| ATCC ® BAA-198 ™ | Multidrug resistant |
| Klabsiella Pneumoniaea | NDM1 |
| ATCC ® BAA-2473 ™ | Carbepenem-resistant |
| | (Imipenem and Ertapenem) |
| Klabsiella Pneumoniaea | KPC$^+$ |
| ATCC ® BAA-2344 ™ | Carbapenem resistant |
| | (Imipenem and Ertapenem) |
| Pseudomonas aeruginosa | Multidrug resistant |
| ATCC ® BAA-2110 ™ | |
| Salmonella serotype Typhi | Resistant to ampicillin Chloramphenicol, |
| ATCC ® 700408 ™ | streptomycin, sulfonamide, tetracycline |
| Acinetobacter baumannii | Multidrug resistant |
| ATCC ® BAA-1793 | |

TABLE 7

Summary of MIC values (μM)

| Bacteria Strain | OMN2 | OMN6 | OMN7 | OMN11 | +10% FBS | | | |
|---|---|---|---|---|---|---|---|---|
| | | | | | OMN2 | OMN6 | OMN7 | OMN11 |
| E. coli Sens. 25922 | 25 | 12.5 | 12.5 | 25 | 25 | 3.3 | 25 | 25 |
| E. coli ESBL BAA-198 | 12.5 | 5 | 10 | 10 | 25 | 5 | 12.5 | 5 |
| E. coli CR BAA-2452 | 20 | 12.5 | 25 | 20 | 20 | 10 | 40 | 10 |
| K. pneu KPC$^+$ BAA-2344 | 12.5 | 5 | 10 | 10 | 50 | 10 | 20 | 10 |

TABLE 7-continued

Summary of MIC values (μM)

| Bacteria Strain | OMN2 | OMN6 | OMN7 | OMN11 | +10% FBS OMN2 | OMN6 | OMN7 | OMN11 |
|---|---|---|---|---|---|---|---|---|
| K. pneu NDM1 BAA-2473 | 100 | 25 | 25 | 50 | 100 | 10 | 40 | 40 |
| P. aeruginosa BAA-2110 | >200 | 20 | 50 | 40 | 100 | 40 | 50 | 40 |
| Salmonella Typhi 700408 | 200 | 100 | 100 | 100 | >200 | 200 | >200 | 200 |
| A. baumannii BAA-1793 | 5 | 2.5 | 2.5 | 5 | 10 | 5 | 10 | 10 |

Example 7

OMN Peptides Minimal Bactericidal Concentration (MBC) Values on Sensitive and Resistant Bacteria In-Vitro In order to determine the Minimal Bactericidal Concentration (MBC) values of the peptides, colony formation of various bacteria strains was monitored and determined after treatment with the peptides of the invention. Multi-Drug Resistant A. baumannii bacteria were cultured with or without OMN6 in increasing concentrations, as is detailed in FIG. 6 and Example 6. Immediately afterwards, samples of each experimental group were diluted to 1×10⁴ to 1×10⁶ as necessary, and further, the samples were plated on appropriate medium-agar plates. All the plates were incubated at 37° C. for 24-48 hours. Colonies were counted and CFU/ml in the original sample, prior to plating, were calculated and determined. An example of the plates, after incubation, is presented in FIG. 7 where the plate on the left side of the image is the CTRL sample treated with DDW and in the right side of the image increasing concentrations of OMN6 are presented, as specified therein. The results show abundant growth of bacteria in the CTRL group, no inhibition of growth is detected in the CTRL, as well as in OMN6 at concentrations of 0.62 μM and 1.25 μM groups. In the groups treated with OMN6 at 2.5 μM, 5 μM and 10 μM the plates are clear, i.e void of colonies.

These results clearly demonstrate the antimicrobial effect of OMN6. Furthermore, the fact that the MIC values (FIG. 6 and Example 6) are very similar to the MBC values (FIG. 7 and Example 7) points to a bactericidal effect of the OMN peptides of the invention. The growth of the bacteria was not merely inhibited but the bacteria were killed upon contact with the peptides.

The experimental system and parameters described here were used to determine the MBC values of OMN2, OMN6, OMN7 and OMN11 on various bacteria strains with and without the supplementation of 10% FBS (Table 6 and Table 8).

TABLE 8

Summary of MBC values (μM)

| Bacteria Strain | OMN2 | OMN6 | OMN7 | OMN11 | +10% FBS OMN2 | OMN6 | OMN7 | OMN11 |
|---|---|---|---|---|---|---|---|---|
| E. coli Sens. 25922 | 25 | 12.5 | 12.5 | 25 | 25 | 3.3 | 25 | 25 |
| E. coli ESBL BAA-198 | 12.5 | 5 | 10 | 10 | 25 | 5 | 12.5 | 5 |
| E. coli CR BAA-2452 | 20 | 12.5 | 25 | 20 | 20 | 10 | 40 | 10 |
| K. pneu KPC⁺ BAA-2344 | 12.5 | 5 | 10 | 10 | 50 | 10 | 20 | 10 |
| K. pneu NDM1 BAA-2473 | 100 | 25 | 25 | 50 | 100 | 10 | 40 | 40 |
| P. aeruginosa BAA-2110 | >200 | 20 | 50 | 40 | 100 | 40 | 50 | 40 |
| Salmonella Typhi 700408 | 200 | 100 | 200 | 200 | >200 | 200 | >200 | 200 |
| A. baumannii BAA-1793 | 5 | 2.5 | 2.5 | 5 | 10 | 5 | 10 | 10 |

The combined results from the MIC experiments and the MBC experiments detailed above show that OMN peptides of the invention are highly effective antimicrobial agents. Treatment with OMN peptides directly leads to the death of resistant bacteria strains. The fact that MIC and MBC values are identical, points to a strong and rapid bactericidal effect. This bactericidal effect lowers the occurrence of resistance development as well as the chance of tolerance.

Example 8

OMN6 Antimicrobial Peptide Preliminary Safety in Mouse Model

The antimicrobial peptide OMN6 was administered to mice in order to evaluate and quantify whether toxic effects are present. OMN6 peptide ($C_{195}H_{332}N_{56}O_{49}S_3$) was administered topically according to concentrations and groups detailed in Table 9.

TABLE 9

OMN6 Preliminary Topical Safety in Mice Experiment Overview

| Treatment | Group | | | | |
|---|---|---|---|---|---|
| | CTRL | OMN6 | OMN6 | OMN6 | OMN6 |
| Topical Administration | Sham | 0.5 mg/kg | 1 mg/kg | 2 mg/kg | 4 mg/kg |
| Food/Water consumption Monitoring | √ | √ | √ | √ | √ |
| Mortality | √ | √ | √ | √ | √ |
| Hemolysis analysis | √ | √ | √ | √ | √ |

Mice approved for this experiment: Outbred Hsd:ICR (CD-1®)—weight 18-20 g. Saline solution (0.9% NaCl) as sham treatment or OMN6 dissolved in saline were administered directly onto the skin of mice after the hair was shaved. A total volume of 16 µl was administered to each animal. In this experiment, the peptide OMN6 of the invention was administered in a single dose, at four different concentrations (mg/kg). Mortality of mice in all experiment groups was monitored in comparison to a Sham (CTRL) group. Food and water consumption, post treatment, was monitored by individual weight measurements once every two days. At the end of the experiment, blood was taken from all animals and 200 µl of blood was separated and plasma was analyzed for erythrocyte hemolysis.

Experimental Map

1. Mice (six per group) were given a single-dose administration on day 1, according to group specification (Table 9). Food and water consumption (weight analysis) along with mortality of mice in all groups were monitored for four days post treatment. At the end of the five day trial, the animals were sacrificed.
2. Free Hgb (hemoglobin) assay was performed on day 5, on all samples from all groups, for erythrocyte hemolysis analysis.
3. Water/food availability, temperature and other conditions remained unchanged between the groups for the entire five day trial.
4. Erythrocyte hemolysis analysis was performed via hemoglobin assay kit (Sigma-Aldrich, 3 Plaut St. Rehovot, Israel).

The results from the topical administration experiment clearly show that OMN6 does not exert any toxic or otherwise adverse effects when it is administered topically. Mortality was not observed in any of the groups throughout the entire 5-day experiment. Clinical signs such as: diarrhea, bloody diarrhea, stand-on-end hair, apathy or restlessness were not observed in any of the groups throughout the entire 5-day experiment. Weight-loss was not observed in any of the groups throughout the entire 5-day experiment, and further, in all cages animals gained weight at a normal rate.

No evidence of hemolysis of erythrocytes was observed in any of the experiment groups. The results strongly suggest that the peptides are highly specific and target only bacteria cells without harming eukaryotic membranes at all.

IP Administration of OMN6:

OMN6 was administered IP to mice in order to evaluate and quantitate any toxic effects if present. OMN6 peptide was administered via intraperitoneal injection according to concentrations and groups detailed in Table 10.

TABLE 10

OMN6 Preliminary IP Safety in Mice Experiment Overview

| Treatment | Group | |
|---|---|---|
| | CTRL | OMN6 |
| IP Administration | Sham (4 mM Sodium Acetate) | 16 mg/kg |
| Food/Water consumption Monitoring | √ | √ |
| Mortality | √ | √ |
| Hemolysis analysis | √ | √ |

Mice used in this experiment: Outbred Hsd: ICR (CD-1®)—weight 18-20 g. Saline solution (0.9% NaCl) supplemented with 4 mM $C_2H_3NaO_2$ (sodium acetate) as sham treatment, or OMN6 dissolved in saline were administered as specified in Table 9 A total volume of 100 µl was administered to each animal. Mortality of mice in experiment group was monitored in comparison to a Sham (CTRL) group. Food and water consumption, post treatment, was monitored by individual weight measurements once every two days. At the end of the experiment, blood was taken from all animals, and a 200 µl volume of complete blood was separated and plasma was analyzed for erythrocyte hemolysis.

Experimental Map

1. Mice (six per group) were given a single-dose administration on day 1, according to group specification (Table 10). Food and water consumption (weight analysis) along with mortality of mice in all groups were monitored for 3 days post treatment. At the end of the four day trial, the animals were sacrificed.
2. Free Hgb (hemoglobin) assay was performed on day 4, on all samples from all groups, for erythrocyte hemolysis analysis.
3. Water/food availability, temperature and other conditions remained unchanged between the groups for the entire four day trial.
4. The Erythrocyte hemolysis analysis was performed via hemoglobin assay kit (Sigma-Aldrich, 3 Plaut St. Rehovot, Israel).

The results clearly show that OMN6 does not exert any toxic or otherwise adverse effects when injected IP into mice. Mortality was not observed in any of the groups throughout the entire four-day experiment. Clinical signs such as: diarrhea, bloody diarrhea, stand-on-end hair, apathy or restlessness were not observed in any of the groups throughout the entire four-day experiment. Weight-loss was not observed in any of the groups throughout the entire four-day experiment, further in all of the cages animals gained weight at a normal rate.

The results demonstrate that the peptides of the invention are safe. No evidence of hemolysis of erythrocytes was observed in any of the experiment groups. Histological analysis was conducted (data not shown). No evidence of pathological changes or aberrations was observed in any of the experiment groups.

Example 9

OMN6 Efficacy in Mouse Model Subcutaneous Infection with *E. coli*

Animals:

Healthy adult female mice weighing 16-20 g were used. CD-I outbred (Harlan Breeding Labs, Jerusalem, Israel)

were used in all experiments. Animals were caged in groups of 5-10 and were maintained on chow (Ralston Purina) and water ad-libitum.

Bacteria:

*Escherichia coli* (ATCC BAA-198) is an extended spectrum beta-lactamase (ESBL) TEM-26 multi drug resistant strain. Stock cultures were grown in Tryptic Soy Broth (TSB) (Becton, Dickinson and company BD. Maryland, USA) at 37°. Colonies were counted after incubation for 24 hours on TSB-agar (BD), and results were expressed as colony forming units (CFU)/ml.

Inoculum:

All broth cultures were adjusted to $1 \times 10^8$ CFU/animal for the challenge dose by adding TSB to a final volume of 50 µl. Bacteria were administered via subcutaneous (SC) injection with tuberculin syringes capped with 29-gauge needles. Recipient animals had the right flank shaved and depilated with hair remover cream (ORNA19, Israel). To inject the inoculum, the needle was inserted SC 1 cm lateral to the thoracic spine and just anterior to the right hind extremity. The needle was tracked anteriorly and SC for 1 cm; then 50 µl of inoculum was injected. OMN6 peptide at 8 mg/kg in a total volume of 80 µl was injected SC after one hour to the same area. All animals appeared well and fully active within 2-4 hours after this procedure. All animals were monitored for food and water consumption, mortality and any other adverse effects for the entire 5-day duration of the experiment.

Evaluation of Bacterial Burden:

A 2 cm$^2$ area of skin was incised and the inner side, where the abscess was located, was scraped with a sterile scalpel. Scraped tissue was filtered through a 40 µm cell-strainer. Filtered mass was collected, centrifuged at 500 RPM for 2 minutes and a sample from the supernatant was plated on TBS-agar plates for 24 hours at 37°. Colonies were then counted and results are presented as CFU/abscess (see FIG. 10A).

Evaluation of Abscesses:

Animals were assessed for the presence and size of abscesses on day 5. The animals were anesthetized (Ketamine 225 mg/kg/Xylazine 6 mg/kg BW IP), the right hind flank area was gently exposed by aseptic technique. Abscesses were recorded and then measured by calipers: the product of the longest diameter (D) and corresponding perpendicular diameter (d) was determined as "abscess size" (D×d) findings presented in mm$^2$ (see FIG. 10B).

Results:

FIG. 10A: The bacteria burden found in the group of animals inoculated with bacteria and treated with a sham-saline treatment was: 300 CFU/mouse The bacteria burden found in the group of animals inoculated with bacteria and treated with OMN6 at 8 mg/kg was 20 CFU/mouse.

The results show 93.3% decrease in bacteria burden, pointing to a strong antimicrobial effect of OMN6 in-vivo. The fact that the measurements were made after five days, points to a powerful and rapid bactericidal effect of OMN6 leading to direct death of almost all the bacteria that were introduced to the mouse. To conclude, a single dose of OMN6 was enough to eliminate the bacteria, significantly reducing the bacteria burden and the formation of an abscess. Accordingly, it is clear that OMN6 is effective in-vivo and has a long lasting effect of a bactericidal nature.

FIG. 10B:

The average size of the abscesses found in the group of animals inoculated with bacteria and treated with a sham-saline treatment was 35.25 mm$^2$ The average size of the abscesses found in the group of animals inoculated with bacteria and treated with OMN6 at 8 mg/kg was 7.25 mm$^2$ The results show 80% decrease in abscess size, pointing to a strong antimicrobial effect of OMN6 in-vivo. Furthermore, the fact that the measurements were made after five days points to a powerful and rapid bactericidal effect of OMN6 leading to direct death of all the bacteria that were introduced to the mouse.

What is claimed is:

1. A cyclic peptide that has an amino acid sequence having at least 95% sequence identity to the amino acid sequence set forth in SEQ ID NO: 6.

2. The cyclic peptide of claim 1, wherein the peptide is as set forth in SEQ ID NO:6.

3. A pharmaceutical composition comprising the cyclic peptide of claim 1.

4. A method of treating a bacterial infection, the method comprising administering the cyclic peptide of claim 1 to a subject in need thereof, wherein the bacterial infection is caused by gram negative bacteria.

5. The pharmaceutical composition of claim 3, wherein the pharmaceutical composition is in a form of a liquid, cream, gel, paste, powder, emulsion, an ointment, a liniment, a lotion, a transdermal system, an injection fluid, a suspension, a film patch or spray.

6. The pharmaceutical composition of claim 3, which is in the form of a capsule or a tablet.

7. A pharmaceutical composition comprising the cyclic peptide of claim 1 in conjunction with one or more anti-inflammatory active agents.

8. A method of overcoming inherent or acquired resistance of a gram negative bacteria to an antibiotic agent, comprising: contacting the gram negative bacteria with the cyclic peptide of claim 1.

9. The method of claim 8, wherein the gram negative bacteria is a member of *Enterobacteriaceae* spp., *Pseudomonas* spp. *Salmonella* spp., or *Acinetobacter* spp., or any combination thereof.

10. A method of disinfecting a cutaneous abscess comprising contacting the cutaneous abscess with the cyclic peptide of claim 1, wherein the infection in the cutaneous abscess is caused by gram negative bacteria.

11. The cyclic peptide according to claim 1, wherein the amino acid sequence has at least 99% sequence identity to the amino acid sequence set forth in SEQ ID NO: 6.

* * * * *

SEQUENCE LISTING

```
<160> NUMBER OF SEQ ID NOS: 33

<210> SEQ ID NO 1
<211> LENGTH: 43
<212> TYPE: PRT
<213> ORGANISM: Artificial Sequence
<220> FEATURE:
<223> OTHER INFORMATION: Artificial modified Cecropin protein

<400> SEQUENCE: 1

Met Cys Gly Trp Leu Lys Lys Ile Gly Lys Lys Ile Glu Arg Val Gly
1               5                   10                  15

Gln His Thr Arg Asp Ala Thr Ile Gln Gly Leu Gly Ile Ala Gln Gln
            20                  25                  30

Ala Ala Asn Val Ala Ala Thr Ala Arg Gly Cys
        35                  40

<210> SEQ ID NO 2
<211> LENGTH: 38
<212> TYPE: PRT
<213> ORGANISM: Artificial Sequence
<220> FEATURE:
<223> OTHER INFORMATION: Artificial modified Cecropin protein
```

```
<400> SEQUENCE: 2

Met Cys Lys Trp Lys Val Phe Lys Lys Ile Glu Met Lys Gly Arg Asn
1               5                   10                  15

Ile Arg Asn Gly Ile Val Lys Ala Gly Pro Ala Ile Ala Val Leu Gly
                20                  25                  30

Glu Ala Lys Ala Leu Cys
            35

<210> SEQ ID NO 3
<211> LENGTH: 39
<212> TYPE: PRT
<213> ORGANISM: Artificial Sequence
<220> FEATURE:
<223> OTHER INFORMATION: Artificial modified Cecropin protein

<400> SEQUENCE: 3

Met Cys Trp Asn Pro Phe Lys Glu Leu Glu Arg Ala Gly Gln Arg Val
1               5                   10                  15

Arg Asp Ala Val Thr Ser Ala Ala Pro Ala Val Ala Thr Val Gly Gln
                20                  25                  30

Ala Ala Ala Ile Ala Arg Cys
            35

<210> SEQ ID NO 4
<211> LENGTH: 39
<212> TYPE: PRT
<213> ORGANISM: Artificial Sequence
<220> FEATURE:
<223> OTHER INFORMATION: Artificial modified Cecropin protein

<400> SEQUENCE: 4

Met Cys Trp Asn Pro Phe Lys Glu Leu Glu Lys Val Gly Gln Arg Val
1               5                   10                  15

Arg Asp Ala Val Ile Ser Ala Gly Pro Ala Val Ala Thr Val Ala Gln
                20                  25                  30

Ala Thr Ala Leu Ala Lys Cys
            35

<210> SEQ ID NO 5
<211> LENGTH: 39
<212> TYPE: PRT
<213> ORGANISM: Artificial Sequence
<220> FEATURE:
<223> OTHER INFORMATION: Artificial modified Cecropin protein

<400> SEQUENCE: 5

Met Cys Trp Asn Pro Phe Lys Glu Leu Glu Arg Ala Gly Gln Arg Val
1               5                   10                  15

Arg Asp Ala Ile Ile Ser Ala Gly Pro Ala Val Ala Thr Val Ala Gln
                20                  25                  30

Ala Thr Ala Leu Ala Lys Cys
            35

<210> SEQ ID NO 6
<211> LENGTH: 40
<212> TYPE: PRT
<213> ORGANISM: Artificial Sequence
<220> FEATURE:
<223> OTHER INFORMATION: Artificial modified Cecropin protein

<400> SEQUENCE: 6

Met Cys Lys Trp Lys Leu Phe Lys Lys Ile Glu Lys Val Gly Gln Asn
```

```
                 1               5                  10                  15
Ile Arg Asp Gly Ile Ile Lys Ala Gly Pro Ala Val Ala Val Val Gly
                20                  25                  30

Gln Ala Thr Gln Ile Ala Lys Cys
            35                  40

<210> SEQ ID NO 7
<211> LENGTH: 38
<212> TYPE: PRT
<213> ORGANISM: Artificial Sequence
<220> FEATURE:
<223> OTHER INFORMATION: Artificial modified Cecropin protein

<400> SEQUENCE: 7

Met Cys Arg Trp Lys Ile Phe Lys Lys Ile Glu Lys Val Gly Gln Asn
1               5                  10                  15

Ile Arg Asp Gly Ile Val Lys Ala Gly Pro Ala Val Ala Val Val Gly
                20                  25                  30

Gln Ala Ala Thr Ile Cys
            35

<210> SEQ ID NO 8
<211> LENGTH: 38
<212> TYPE: PRT
<213> ORGANISM: Artificial Sequence
<220> FEATURE:
<223> OTHER INFORMATION: Artificial modified Cecropin protein

<400> SEQUENCE: 8

Met Cys Arg Trp Lys Ile Phe Lys Lys Ile Glu Lys Met Gly Arg Asn
1               5                  10                  15

Ile Arg Asp Gly Ile Val Ala Ala Gly Pro Ala Ile Glu Val Leu Gly
                20                  25                  30

Ser Ala Lys Ala Ile Cys
            35

<210> SEQ ID NO 9
<211> LENGTH: 38
<212> TYPE: PRT
<213> ORGANISM: Artificial Sequence
<220> FEATURE:
<223> OTHER INFORMATION: Artificial modified Cecropin protein

<400> SEQUENCE: 9

Met Cys Lys Trp Lys Ile Phe Lys Lys Ile Glu Lys Val Gly Arg Asn
1               5                  10                  15

Ile Arg Asn Gly Ile Ile Lys Ala Gly Pro Ala Val Ala Val Leu Gly
                20                  25                  30

Glu Ala Lys Ala Leu Cys
            35

<210> SEQ ID NO 10
<211> LENGTH: 42
<212> TYPE: PRT
<213> ORGANISM: Artificial Sequence
<220> FEATURE:
<223> OTHER INFORMATION: Artificial modified Cecropin protein

<400> SEQUENCE: 10

Met Cys Gly Trp Leu Lys Lys Ile Gly Lys Lys Ile Glu Arg Val Gly
1               5                  10                  15

Gln His Thr Arg Asp Ala Thr Ile Gln Gly Leu Gly Ile Ala Gln Gln
```

```
            20                  25                  30

Ala Ala Asn Val Ala Ala Thr Ala Arg Cys
        35                  40

<210> SEQ ID NO 11
<211> LENGTH: 34
<212> TYPE: PRT
<213> ORGANISM: Artificial Sequence
<220> FEATURE:
<223> OTHER INFORMATION: Artificial modified Cecropin protein

<400> SEQUENCE: 11

Met Cys Ser Trp Leu Ser Lys Thr Ala Lys Lys Leu Glu Asn Ser Ala
1               5                   10                  15

Lys Lys Arg Ile Ser Glu Gly Ile Ala Ile Ala Ile Gln Gly Gly Pro
            20                  25                  30

Arg Cys

<210> SEQ ID NO 12
<211> LENGTH: 40
<212> TYPE: PRT
<213> ORGANISM: Sarcophaga peregrina

<400> SEQUENCE: 12

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg Gly
        35                  40

<210> SEQ ID NO 13
<211> LENGTH: 35
<212> TYPE: PRT
<213> ORGANISM: Hyalophora cecropia

<400> SEQUENCE: 13

Lys Trp Lys Val Phe Lys Lys Ile Glu Met Lys Gly Arg Asn Ile Arg
1               5                   10                  15

Asn Gly Ile Val Lys Ala Gly Pro Ala Ile Ala Val Leu Gly Glu Ala
            20                  25                  30

Lys Ala Leu
        35

<210> SEQ ID NO 14
<211> LENGTH: 36
<212> TYPE: PRT
<213> ORGANISM: Manduca sexta

<400> SEQUENCE: 14

Trp Asn Pro Phe Lys Glu Leu Glu Arg Ala Gly Gln Arg Val Arg Asp
1               5                   10                  15

Ala Val Thr Ser Ala Ala Pro Ala Val Ala Thr Val Gly Gln Ala Ala
            20                  25                  30

Ala Ile Ala Arg
        35

<210> SEQ ID NO 15
<211> LENGTH: 36
<212> TYPE: PRT
<213> ORGANISM: Hyalophora cecropia
```

-continued

<400> SEQUENCE: 15

Trp Asn Pro Phe Lys Glu Leu Glu Lys Val Gly Gln Arg Val Arg Asp
1               5                   10                  15

Ala Val Ile Ser Ala Gly Pro Ala Val Ala Thr Val Ala Gln Ala Thr
            20                  25                  30

Ala Leu Ala Lys
        35

<210> SEQ ID NO 16
<211> LENGTH: 36
<212> TYPE: PRT
<213> ORGANISM: Antheraea pernyi

<400> SEQUENCE: 16

Trp Asn Pro Phe Lys Glu Leu Glu Arg Ala Gly Gln Arg Val Arg Asp
1               5                   10                  15

Ala Ile Ile Ser Ala Gly Pro Ala Val Ala Thr Val Ala Gln Ala Thr
            20                  25                  30

Ala Leu Ala Lys
        35

<210> SEQ ID NO 17
<211> LENGTH: 37
<212> TYPE: PRT
<213> ORGANISM: Hyalophora cecropia

<400> SEQUENCE: 17

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35

<210> SEQ ID NO 18
<211> LENGTH: 35
<212> TYPE: PRT
<213> ORGANISM: Bombyx mori

<400> SEQUENCE: 18

Arg Trp Lys Ile Phe Lys Lys Ile Glu Lys Val Gly Gln Asn Ile Arg
1               5                   10                  15

Asp Gly Ile Val Lys Ala Gly Pro Ala Val Ala Val Val Gly Gln Ala
            20                  25                  30

Ala Thr Ile
        35

<210> SEQ ID NO 19
<211> LENGTH: 35
<212> TYPE: PRT
<213> ORGANISM: Bombyx mori

<400> SEQUENCE: 19

Arg Trp Lys Ile Phe Lys Lys Ile Glu Lys Met Gly Arg Asn Ile Arg
1               5                   10                  15

Asp Gly Ile Val Ala Ala Gly Pro Ala Ile Glu Val Leu Gly Ser Ala
            20                  25                  30

Lys Ala Ile
        35

<210> SEQ ID NO 20
<211> LENGTH: 35
<212> TYPE: PRT
<213> ORGANISM: Antheraea pernyi

<400> SEQUENCE: 20

Lys Trp Lys Ile Phe Lys Lys Ile Glu Lys Val Gly Arg Asn Ile Arg
1               5                   10                  15

Asn Gly Ile Ile Lys Ala Gly Pro Ala Val Ala Val Leu Gly Glu Ala
            20                  25                  30

Lys Ala Leu
        35

<210> SEQ ID NO 21
<211> LENGTH: 39
<212> TYPE: PRT
<213> ORGANISM: Drosophila melanogaster

<400> SEQUENCE: 21

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg
        35

<210> SEQ ID NO 22
<211> LENGTH: 31
<212> TYPE: PRT
<213> ORGANISM: Sus scrofa domesticus

<400> SEQUENCE: 22

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 23
<211> LENGTH: 129
<212> TYPE: DNA
<213> ORGANISM: Artificial Sequence
<220> FEATURE:
<223> OTHER INFORMATION: Artificial modified Cecropin DNA

<400> SEQUENCE: 23
atgtgcggct ggctgaaaaa aattggcaaa aaaattgaac gcgtgggcca gcatacccgc      60
gatgcgacca ttcagggcct gggcattgcg cagcaggcgg cgaacgtggc ggcgaccgcg     120
cgcggctgc                                                             129

<210> SEQ ID NO 24
<211> LENGTH: 117
<212> TYPE: DNA
<213> ORGANISM: Artificial Sequence
<220> FEATURE:
<223> OTHER INFORMATION: Artificial modified Cecropin DNA

<400> SEQUENCE: 24
atgtgcaaat ggaaagtgtt taaaaaaatt gaaaaaatgg ccgcaacat tcgcaacggc       60 attgtgaaag cgggcccggc gattgcggtg ctgggcgaag cgaaagcgct gggctgc        117

```
<210> SEQ ID NO 25
<211> LENGTH: 120
<212> TYPE: DNA
<213> ORGANISM: Artificial Sequence
<220> FEATURE:
<223> OTHER INFORMATION: Artificial modified Cecropin DNA

<400> SEQUENCE: 25
atgtgctgga acccgtttaa agaactggaa cgcgcgggcc agcgcgtgcg cgatgcggtg      60
attagcgcgg cgccggcggt ggcgaccgtg ggccaggcgg cggcgattgc gcgcggctgc     120

<210> SEQ ID NO 26
<211> LENGTH: 123
<212> TYPE: DNA
<213> ORGANISM: Artificial Sequence
<220> FEATURE:
<223> OTHER INFORMATION: Artificial modified Cecropin DNA

<400> SEQUENCE: 26
atgtgctgga acccgtttaa agaactggaa aaagtgggcc agcgcgtgcg cgatgcggtg      60
attagcgcgg gcccggcggt ggcgaccgtg gcgcaggcga ccgcgctggc gaaaggcaaa     120
tgc                                                                    123

<210> SEQ ID NO 27
<211> LENGTH: 117
<212> TYPE: DNA
<213> ORGANISM: Artificial Sequence
<220> FEATURE:
<223> OTHER INFORMATION: Artificial modified Cecropin DNA

<400> SEQUENCE: 27
atgtgctgga acccgtttaa agaactggaa cgcgcgggcc agcgcgtgcg cgatgcgatt      60
attagcgcgg gcccggcggt ggcgaccgtg gcgcaggcga ccgcgctggc gaaatgc        117

<210> SEQ ID NO 28
<211> LENGTH: 123
<212> TYPE: DNA
<213> ORGANISM: Artificial Sequence
<220> FEATURE:
<223> OTHER INFORMATION: Artificial modified Cecropin DNA

<400> SEQUENCE: 28
atgtgcaaat ggaaactgtt taaaaaaatt gaaaaagtgg ccagaacat tcgcgatggc       60 attattaaag cgggcccggc ggtggcggtg gtgggccagg cgacccagat tgcgaaaggc    120
tgc                                                                    123

<210> SEQ ID NO 29
<211> LENGTH: 114
<212> TYPE: DNA
<213> ORGANISM: Artificial Sequence
<220> FEATURE:
<223> OTHER INFORMATION: Artificial modified Cecropin DNA

<400> SEQUENCE: 29
atgtgccgct ggaaaatttt taaaaaaatt gaaaaagtgg ccagaacat tcgcgatggc       60 attgtgaaag cgggcccggc ggtggcggtg gtgggccagg cggcgaccat ttgc            114

<210> SEQ ID NO 30
<211> LENGTH: 120
<212> TYPE: DNA
<213> ORGANISM: Artificial Sequence
```

```
<220> FEATURE:
<223> OTHER INFORMATION: Artificial modified Cecropin DNA

<400> SEQUENCE: 30
atgtgccgct ggaaaatttt taaaaaaatt gaaaaaatgg ccgcaacat tcgcgatggc      60 attgtgaaag cgggcccggc gattgaagtg ctgggcagcg cgaaagcgat tggcaaatgc    120

<210> SEQ ID NO 31
<211> LENGTH: 114
<212> TYPE: DNA
<213> ORGANISM: Artificial Sequence
<220> FEATURE:
<223> OTHER INFORMATION: Artificial modified Cecropin DNA

<400> SEQUENCE: 31
atgtgcaaat ggaaaatttt taaaaaaatt gaaaaagtgg ccgcaacat tcgcaacggc      60 attattaaag cgggcccggc ggtggcggtg ctgggcgaag cgaaagcgct gtgc           114

<210> SEQ ID NO 32
<211> LENGTH: 138
<212> TYPE: DNA
<213> ORGANISM: Artificial Sequence
<220> FEATURE:
<223> OTHER INFORMATION: Artificial modified Cecropin DNA

<400> SEQUENCE: 32
atgtgcagcg aagcgggctg gctgaaaaaa attggcaaaa aaattgaacg cgtgggccag     60
catacccgcg atgcgaccat tcagggcctg ggcattgcgc agcaggcggc gaacgtggcg    120
gcgaccgcgc gcggctgc                                                  138

<210> SEQ ID NO 33
<211> LENGTH: 102
<212> TYPE: DNA
<213> ORGANISM: Artificial Sequence
<220> FEATURE:
<223> OTHER INFORMATION: Artificial modified Cecropin DNA

<400> SEQUENCE: 33
atgtgcagct ggctgagcaa aaccgcgaaa aaactggaaa acagcgcgaa aaaacgcatt     60
agcgaaggca ttgcgattgc gattcagggc ggcccgcgct gc                       102
```